US011213595B2

(12) United States Patent
Choi et al.

(10) Patent No.: US 11,213,595 B2
(45) Date of Patent: Jan. 4, 2022

(54) ANTIGEN RESPONSIVE ANTIBODY-FLUORESCENT DYE CONJUGATE AND METHOD FOR FLUORESCENCE DETECTION AND IMAGING OF TARGET CELL USING THE SAME

(71) Applicant: National Cancer Center, Gyeonggi-do (KR)

(72) Inventors: Yong-Doo Choi, Gyeonggi-do (KR); Hyun-Jin Kim, Gyeonggi-do (KR)

(73) Assignee: National Cancer Center, Gyeonggi-Do (KR)

( * ) Notice: Subject to any disclaimer, the term of this patent is extended or adjusted under 35 U.S.C. 154(b) by 0 days.

(21) Appl. No.: 16/138,371

(22) Filed: Sep. 21, 2018

(65) Prior Publication Data

US 2019/0091349 A1    Mar. 28, 2019

Related U.S. Application Data

(63) Continuation of application No. PCT/KR2017/002924, filed on Mar. 20, 2017.

(30) Foreign Application Priority Data

Mar. 29, 2016    (KR) .................... 10-2016-0037411

(51) Int. Cl.
| | |
|---|---|
| *A61K 49/00* | (2006.01) |
| *G01N 33/58* | (2006.01) |
| *C07K 16/18* | (2006.01) |
| *C07K 16/28* | (2006.01) |
| *G01N 33/574* | (2006.01) |
| *C07K 16/22* | (2006.01) |
| *C07K 16/30* | (2006.01) |
| *C07K 16/32* | (2006.01) |

(52) U.S. Cl.
CPC ...... *A61K 49/0058* (2013.01); *A61K 49/0028* (2013.01); *A61K 49/0039* (2013.01); *A61K 49/0043* (2013.01); *C07K 16/18* (2013.01); *C07K 16/22* (2013.01); *C07K 16/2863* (2013.01); *C07K 16/2878* (2013.01); *C07K 16/2884* (2013.01); *C07K 16/2887* (2013.01); *C07K 16/3069* (2013.01); *C07K 16/3092* (2013.01); *C07K 16/32* (2013.01); *G01N 33/57492* (2013.01); *G01N 33/582* (2013.01); *C07K 2317/77* (2013.01)

(58) Field of Classification Search
None
See application file for complete search history.

(56) References Cited

U.S. PATENT DOCUMENTS

| | | | |
|---|---|---|---|
| 2006/0280688 A1 | 12/2006 | Kovar et al. | |
| 2010/0203554 A1* | 8/2010 | Enderle | C12Q 1/42 435/7.4 |
| 2011/0237942 A1 | 9/2011 | Zako et al. | |
| 2013/0039861 A1 | 2/2013 | Regino et al. | |
| 2014/0329228 A1* | 11/2014 | Ueda | G01N 33/542 435/5 |

FOREIGN PATENT DOCUMENTS

| | | |
|---|---|---|
| CN | 101679510 A | 3/2010 |
| CN | 103917872 A | 7/2014 |
| EP | 2155786 A2 | 2/2010 |
| EP | 2775305 A1 | 9/2014 |
| KR | 10-1169243 B1 | 8/2012 |
| KR | 10-2014-0102968 A | 8/2014 |
| KR | 10-1452819 B1 | 10/2014 |
| KR | 10-1603456 B1 | 3/2016 |
| KR | 10-2016-0037411 A | 4/2016 |
| WO | 2015/170878 A1 | 11/2015 |

OTHER PUBLICATIONS

Ogawa et al. In vivo molecular imaging of cancer with a quenching near-infrared fluorescent probe using conjugates of monoclonal antibodies and indocyanine green. 2009 Cancer Res. 69: 1268-1272. (Year: 2009).*
Amino acids reference chart. Sigma-Aldrich website, <sigmaaldrich.com/life-science/metabolomics/learning-center/amino-acid-reference-chart.html>. Accessed Sep. 16, 2019. (Year: 2019).*
Alford et al. Fluorescence lifetime imaging of activatable target specific molecular probes. 2010 Contrast Media Mol. Imaging 5: 1-8. (Year: 2010).*
Partial Supplementary European Search Report for European Patent Application No. 17775708.5, dated Feb. 14, 2020, 16 pages.
Kim, Hyunjin et al., "Antigen-responsive molecular sensor enables real-time tumor-specific imaging", Theranostics, vol. 7, Issue 4, pp. 952-961 (2017).

(Continued)

*Primary Examiner* — Jennifer Lamberski
(74) *Attorney, Agent, or Firm* — Mintz Levin Cohn Ferris Glovsky and Popeo, P.C.; Steven M. Jensen; Joohee Lee

(57) ABSTRACT

The present invention relates to an antibody-fluorescent dye conjugate capable of cancer cell-specific fluorescence imaging diagnosis. The fluorescent dye comprises a covalently labeled antibody and is quenched by interaction with an amino acid residue such as tryptophan, tyrosine, histidine, and methionine in the antibody and upon binding of the antibody to an antigen present on a cell surface to emit fluorescence, whereby cells having a target antigen thereon can be imaged for diagnosis. When using the antibody-fluorescent dye conjugate according to the present invention during in vitro cell assays, high-throughput screening of cells, and cytodiagnosis based on microfluidics, the presence of cancer cells having a specific antigen expressed thereon can be detected at high specificity and sensitivity without a washing process, and the position of primary and metastatic cancer cells can be detected at high contrast within a short time.

7 Claims, 22 Drawing Sheets

(56) References Cited

OTHER PUBLICATIONS

Pancuk-Voloshina, N. et al., "Alexa Dyes, a Series of New Fluorescent Dyes that Yield Exceptionally Bright, Photostable Conjugates", The Journal of Histochemistry & Cytochemistry, vol. 47(9): 1179-1188 (1999).

Ueda, H. et al., "From Fluorescence Polarization to Quenchbody: Recent Progress in Fluorescent Reagentless Biosensors Based on Antibody and Other Binding Proteins", Biochimica et Biophysica Acta (BBA)—Proteins & Proteomics (Nov. 2014) 37 pages.

International Search Report for International Patent Application No. PCT/KR2017/002924, dated Jun. 30, 2017 (2 pages).

International Search Report for International Patent Application No. PCT/KR2017/002924, dated Jun. 30, 2017, Korean language (3 pages).

Nakajima, T. et al., "Targeted, Activatable, In Vivo Fluorescence Imaging of Prostate-specific Membrane Antigen (PSMA)-positive Tumors Using the Quenched Humanized J591 Antibody-ICG Conjugate", Bioconjug Chem. (Aug. 17, 2011) 22(8): 1700-1705.

Kobayashi, H. et al., "New Strategies for Fluorescent Probe Design in Medical Diagnostic Imaging", Chem. Rev. (May 12, 2010) 110(5): 2620-2640.

Abe, R. et al., "Quenchbodies: Quench-Based Anitbody Probes That Show Antigen-Dependent Fluorescence", Journal of the American Chemical Society (Nov. 2011) 39 pages.

Kobayashi, H. et al., "Target-cancel cell specific activatable fluorescence imaging Probes: Rational Design and in vivo Applications", Acc Chem Res. (Feb. 15, 2011) 44(2): 83-90.

Terwisscha van Scheltinga, A. et al., "Introperative Near-Infrared Fluorescence Tumor Imaging with Vascular Endothelial Growth Factor and Human Epidermal Growth Factor Receptor 2 Targeting Antibodies", The Journal of Nuclear Medicine, vol. 52, No. 11 (Nov. 2011) 9 pages.

Even-Desrumeaux, K. et al., "State of the Art in Turmor Antigen and Biomarker Discovery", Cancers (2011) 3, pp. 2554-2596.

European Office Action for application No. 17775708.5 dated Mar. 22, 2021.

Choi et al., "Targeted zwitterionic near-infrared fluorophores for improved optical imaging", Nature Biotechnology vol. 31, pp. 148-153 (2013), Published: Jan. 6, 2013.

\* cited by examiner

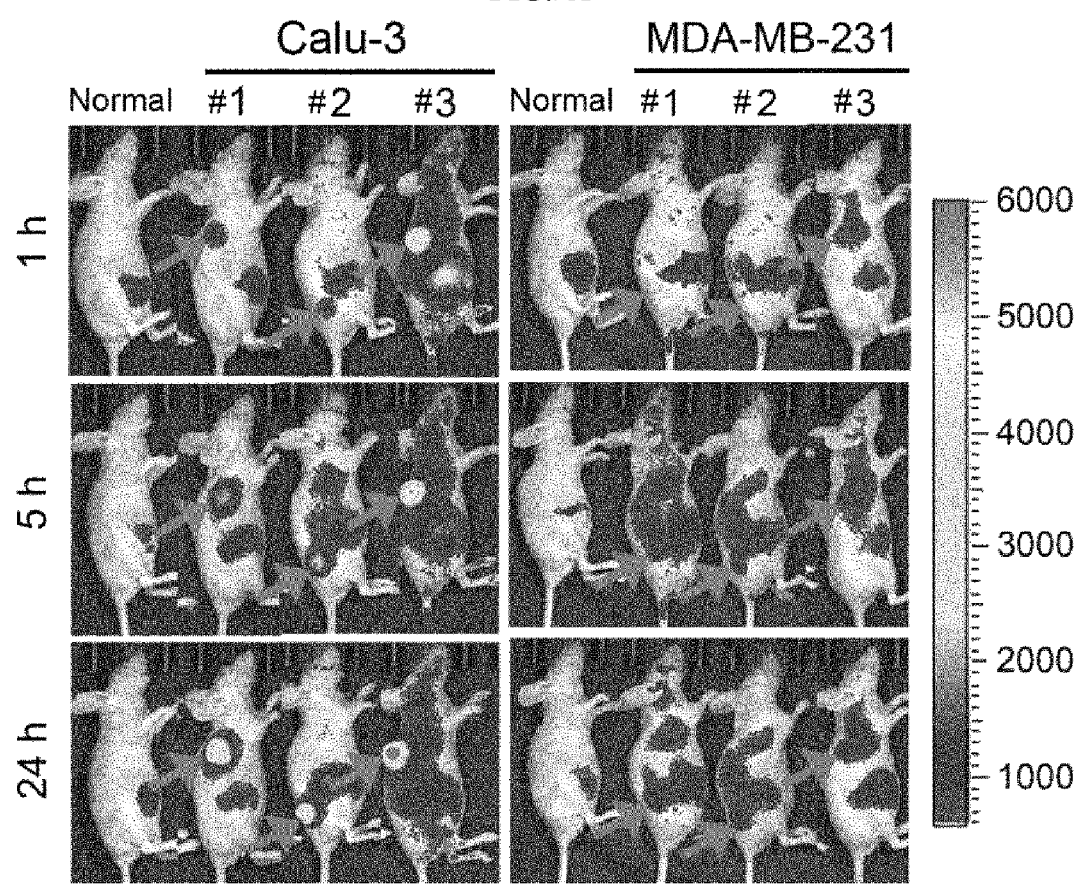

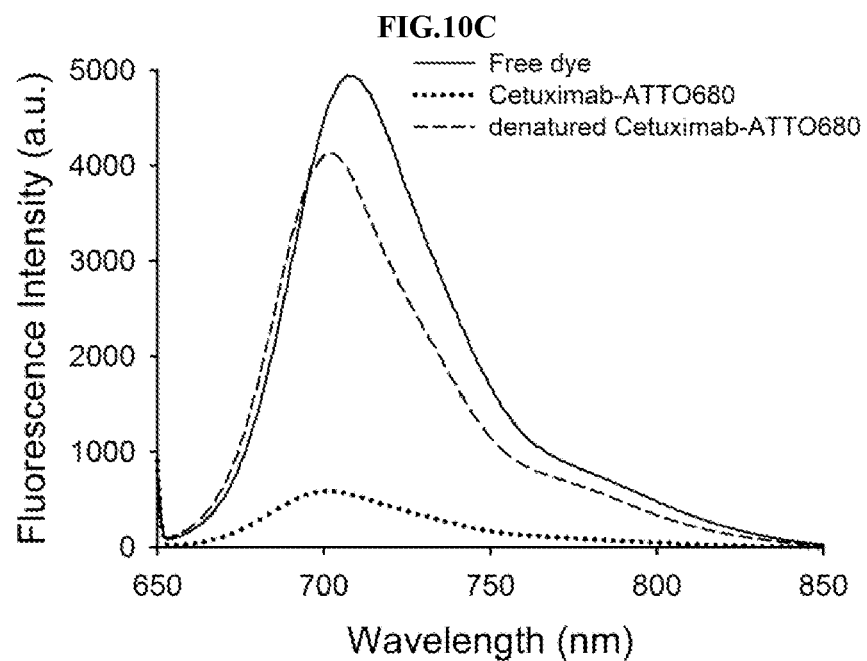
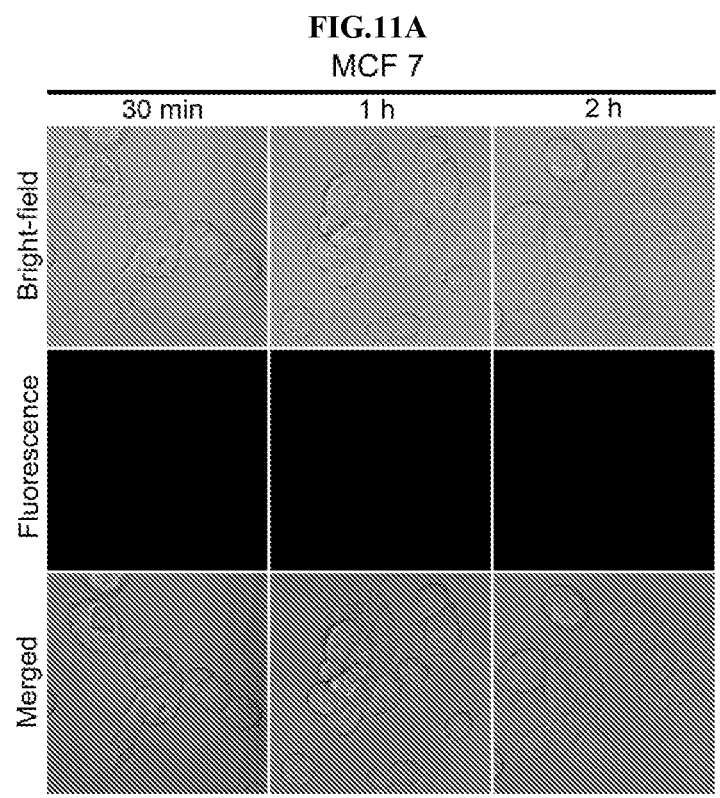

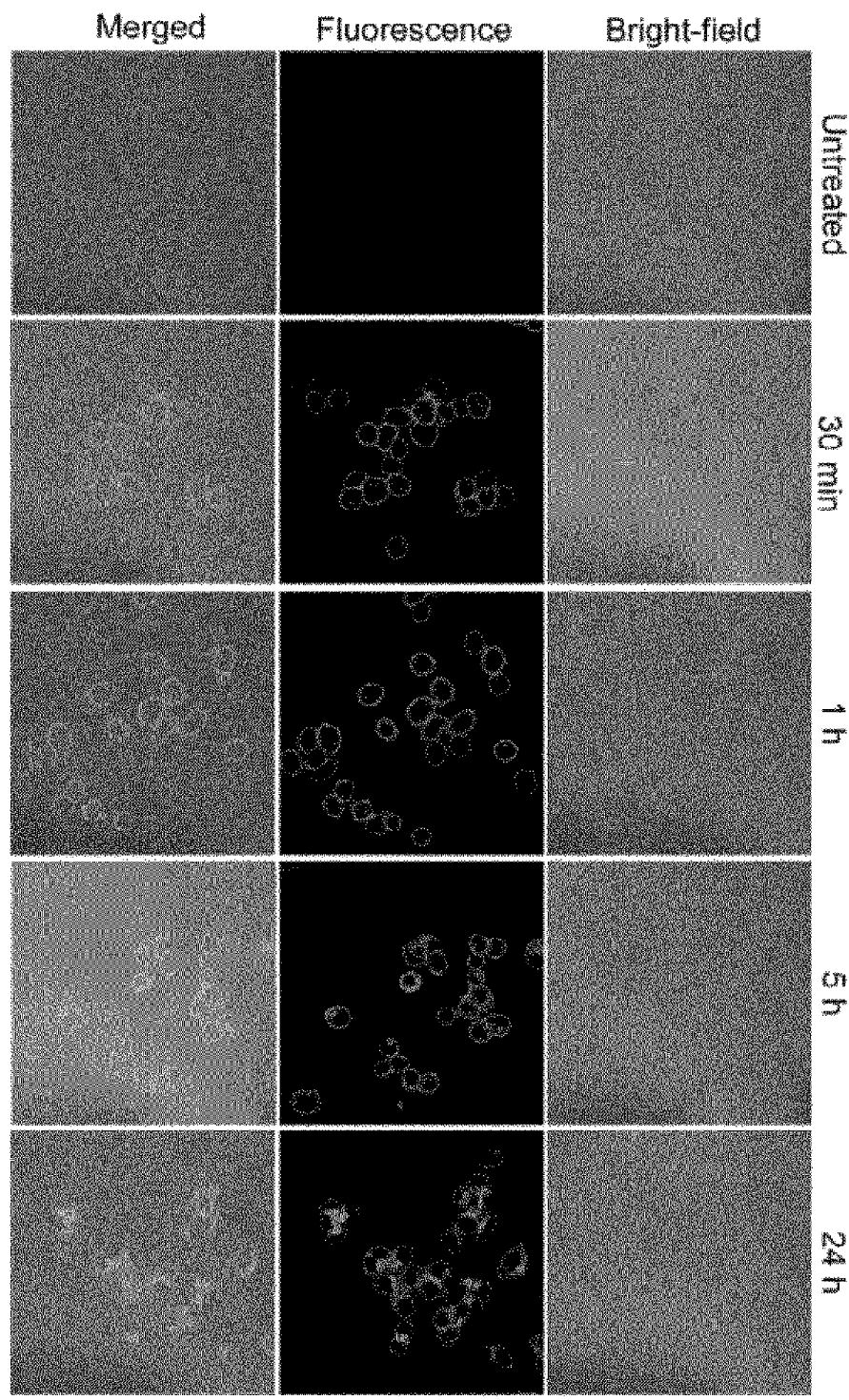

Anti-VEGF-ATTO680 Conjugate

ANTIGEN RESPONSIVE ANTIBODY-FLUORESCENT DYE CONJUGATE AND METHOD FOR FLUORESCENCE DETECTION AND IMAGING OF TARGET CELL USING THE SAME

CROSS-REFERENCE TO RELATED APPLICATIONS

This application is a continuation of International Application No. PCT/KR2017/002924 filed on Mar. 20, 2017, which claims priority to Korean Application No. 10-2016-0037411 filed on Mar. 29, 2016. The applications are incorporated herein by reference.

TECHNICAL FIELD

The present invention relates to production of an antigen responsive antibody-fluorescent dye conjugate and a target cell-specific fluorescence imaging method using the same.

BACKGROUND ART

Due to a great advantage that real-time image acquisition is possible while having high sensitivity as compared with magnetic resonance imaging, nuclear medicine imaging, and ultrasound imaging, a fluorescent imaging technique is evaluated as the most powerful tool which is capable of identifying, in real-time, a location of a lesion such as cancer and removing the lesion during surgery. Furthermore, as systems capable of realizing a near-infrared fluorescence imaging function in endoscopic and laparoscopic equipment have become increasingly commercialized in recent years, it is expected that a procedure using fluorescence imaging will be widely used in patient procedures in the future.

An antibody is capable of specifically binding to a receptor or antigen present on a surface of a cell with high binding ability. Thus, various antibody-fluorescent dye conjugates have been developed and used for target cell-specific fluorescence imaging diagnosis. Antibody-fluorescent dye conjugates which have been developed in the related art have an advantage of high binding specificity to targeted cancer cells. However, for the antibody-fluorescent dye conjugates in the related art, both case of being bound to target cells and case of being near the target cells emit a strong fluorescent signal, and thus it is not possible to distinguish whether the conjugates are bound to the target cells. Therefore, in order to detect a target cell through fluorescence imaging, an antibody-fluorescent dye conjugate which is not bound to the target cell has to be removed through a washing process, thereby removing a background signal emitted from an antibody that is not bound to the target cell, which makes it possible to obtain a fluorescent image with high contrast. That is, in an in vitro cell experiment for detecting a fluorescent image of a specific cell, after a cell or a living body tissue is treated with an antibody-fluorescent dye conjugate, a washing process is necessarily performed to remove a conjugate which is not bound to a target cell, and a fluorescent image is obtained, which is troublesome. In particular, the washing process acts as a major limitation for a case where due to a small amount of cells to be analyzed, loss of cells with washing is concerned, a case where an analysis time is increased due to the washing process in a high-throughput drug screening, a case of suspension cells, or a case of intending to image an interaction between an antibody and a cell in real-time. In addition, in a case of diagnosing cancer or bacteria using a microfluidics system, it is often difficult to perform a washing process. Thus, there is a demand for development of an antibody-fluorescent dye conjugate which is capable of obtaining a fluorescent image with good contrast without performing a washing process.

A characteristic that both an antibody-fluorescent dye conjugate which is bound to a target cell and the antibody-fluorescent dye conjugate which is not bound to the target cell emit a strong fluorescent signal becomes more problematic in a case where the antibody-fluorescent dye is intravenously administered to a patient in order to diagnose a location of cancer with fluorescence imaging during surgery. The antibody-fluorescent dye conjugate having a large molecular weight has a long blood half-life of a few days to a few weeks, and thus keeps a background noise signal high while circulating in blood for a long time. Nevertheless, due to being not possible to artificially remove the antibody-fluorescent dye conjugate present in blood, there is a problem that a fluorescent image having a high tumor-to-background ratio can be obtained only in a case where the fluorescent image is obtained after waiting a few days to a few weeks until antibody-fluorescent dye conjugates present in normal tissues or bloodstream are removed sufficiently.

In order to solve these problems, Dr. Hisataka Kobayashi at the National Cancer Institute developed a target cell-specific antibody-fluorescent dye conjugate. In the target cell-specific antibody-fluorescent dye conjugate, a plurality of near-infrared fluorescent dyes are bound to one antibody so that distances among the fluorescent dyes are sufficiently short to one another, and a fluorescent signal is not emitted due to quenching by a mechanism of fluorescence resonance energy transfer (FRET) occurring among the fluorescent dyes. Outside targeted cancer cells, the antibody-fluorescent dye conjugate is in a quenched state. On the other hand, in a case where the target cell-specific antibody-fluorescent dye conjugate binds to a surface of a cancer cell and is introduced into a lysosome in the cancer cell by receptor-mediated endocytosis, the antibody is completely degraded by enzymes in the lysosome and distances among the fluorescent dyes also become long from one another. Thus, a quenching effect due to a FRET action disappears, and, from this point on, a strong fluorescent signal can be emitted. Therefore, using the target cell-specific antibody-fluorescent dye conjugate, targeted cancer cells can be detected as a high tumor-to-background ratio. However, even after binding to a surface of a cancer cell, the target cell-specific antibody-fluorescent dye conjugate can emit a strong fluorescent signal only in a case where the conjugate is introduced in the cancer cell and degraded by enzymes in a lysosome. Thus, it takes a long time during such processes (that is, binding→intracellular migration→lysosomal degradation). In particular, depending on a type of a cancer cell, a time taken for an antigen present on a surface to migrate into the cancer cell is often 12 hours or longer, and it takes time for the conjugate to be degraded in a lysosome in the cell. Thus, there is a disadvantage that a fluorescent image has to be obtained after waiting at least one day following administration of the target cell-specific antibody-fluorescent dye conjugate. Furthermore, among antigens present on cell surfaces, in a case of antigens that do not allow endocytosis into cells, an antibody conjugate cannot migrate to a lysosome. Thus, there is a problem that the target cell-specific antibody-fluorescent dye conjugate cannot be used for fluorescence imaging diagnosis of such antigens. In addition, due to this disadvantage, the target cell-specific antibody-fluorescent dye conjugate is not suitable for obtaining an image with high contrast in an ex-vivo or in vitro cell experiment.

SUMMARY

An object of the present invention is to provide an antigen responsive antibody-fluorescent dye conjugate which has high binding specificity to a specific antigen present on a cancer cell surface and in which fluorescence that has been quenched, that is, a quenching effect disappears immediately upon binding to a target antigen present on the cell surface and a strong fluorescent signal is emitted, so that a cancer cell can be imaged and detected through fluorescence imaging within a short time without a washing process.

In addition, another object of the present invention is to provide a composition for diagnosing or detecting cancer through fluorescence imaging, the composition comprising the antibody-fluorescent dye conjugate according to the present invention as an active ingredient.

In addition, still another object of the present invention is to provide a method for providing information for cancer detection or diagnosis through fluorescence imaging, the method comprising a step of treating a sample with the antibody-fluorescent dye conjugate according to the present invention to obtain a fluorescent signal image.

In order to achieve the above-mentioned objects, the present invention provides an antigen responsive antibody-fluorescent dye conjugate which allows imaging diagnosis of a cell having a target antigen on a surface thereof, the conjugate comprising an antibody covalently labeled with a fluorescent dye, in which the fluorescent dye is quenched by interaction with a residue selected from the group consisting of tryptophan, tyrosine, histidine, and methionine in the antibody, and is dequenched to emit fluorescence in a case where the antibody binds to the antigen present on the surface of the cell.

In an embodiment of the present invention, the antigen to which the antibody binds may be selected from the group consisting of epidermal growth factor receptor (EGFR, HER1), human epidermal growth factor receptor 2 (HER2), human epidermal growth factor receptor 3 (HER3, ERBB-3), human epidermal growth factor receptor 4 (HER4, ERBB-4), epithelial cell adhesion molecule (EpCam), CD19, CD20, CD22 (Siglec-2), CD30 (TNFRSF1), CD33 (Siglec-3), CD44, CD44v6, CD52, CD56 (NCAM), CD152 (CTLA4), mucin 1 (MUC1), carcinoembryonic antigen (CEA), LEWIS Y, prostate-specific membrane antigen (PSMA), tumor-associated glycoprotein 72 (TAG-72), GD2 ganglioside, GD3 ganglioside, human leukocyte antigen-DR10 (HLA-DR10), insulin-like growth factor 1 receptor (IGF1R), tumor-associated antigen L6 (TAL6), tumor-necrosis factor-related apoptosis-inducing ligand receptor 2 (TRAILR2), vascular endothelial growth factor (VEGF), vascular endothelial growth factor receptor 2 (VEGFR2), platelet-derived growth factor receptor alpha (PDFGRA), hepatocyte growth factor receptor (HGFR), Alpha-v beta-3, Folate receptor, EGF-like domain-containing protein 7 (EGFL7), Fibroblast activation protein alpha (FAP), Carbonic anhydrase 9 (CA9/CAIX), and Vimentin.

In an embodiment of the present invention, the antibody may be selected from the group consisting of Cetuximab (Erbitux), Panitumumab (Vectibix), Necitumumab (Portrazza), Imgatuzumab, Matuzumab, Nimotuzumab, Futuximab, and Zalutumumab which are antibodies to EGFR; Trastuzumab (Herceptin) and Pertuzumab (Perjeta) which are antibodies to HER2; Duligotumab, Patritumab, and Seribantumab which are antibodies to HER3; Bevacizumab (Avastin) which is an antibody to VEGF-A; Catumaxomab (Removab) and Adecatumumab (MT201) which are antibodies to EpCam; Cixutumumab (IMC-A12), Figitumumab, Ganitumab, Robatumuma, Teprotumumab, and Dalotuzumab which are antibodies to IGF1R; Conatumumab (AMG 655), Drozitumab, Lexatumumab, and Tigatuzumab which are antibodies to TRAILR2; Rituximab (Rituxan), Ibritumomab tiuxetan (Zevalin), Tositumomab (Bexxar), Ofatumumab (Arzerra), Ocaratuzumab, Ublituximab, and Obinutuzumab which are antibodies to CD20; Epratuzumab (LymphoCide), Inotuzumab, and Narnatumab which are antibodies to CD22; Brentuximab and Iratumumab which are antibodies to CD30; Gentuzumab (Mylotarg) and Lintuzumab which are antibodies to CD33; Bivatuzumab which is an antibody to CD44v6; Alemtuzumab (Campath) which is an antibody to CD52; Dinutuximab (Unituxin) which is an antibody to GD2 ganglioside; Ecromeximab which is an antibody to GD3 ganglioside; Olaratumab which is an antibody to platelet-derived growth factor receptor alpha (PDFGRA); Emibetuzumab which is an antibody to hepatocyte growth factor receptor (HGFR); Etaracizumab (Abegrin) which is an antibody to Alpha-v beta-3; Farletuzumab which is an antibody to Folate receptor alpha; Parsatuzumab which is an antibody to EGF-like domain-containing protein 7 (EGFL7); Sibrotuzumab which is an antibody to Fibroblast activation protein alpha (FAP); Girentuximab (Rencarex) which is an antibody to Carbonic anhydrase 9 (CA9/CAIX), anti-CD44, and anti-Vimentin.

In an embodiment of the present invention, the fluorescent dye may be a fluorescent dye having, as a basic skeleton, rhodamine, coumarin, EvoBlue, oxazine, carbopyronine, naphthalene, biphenyl, anthracene, phenanthrene, pyrene, or carbazole, or a derivative of the fluorescent dye.

In an embodiment of the present invention, the fluorescent dye may be selected from the group consisting of Fluorescein, CR110: Carboxyrhodamine 110: Rhodamine Green (trade name), TAMRA: carboxytetramethylrhodamine: TMR, Carboxyrhodamine 6G: CR6G, BODIPY FL (trade name): 4,4-difluoro-5,7-dimethyl-4-bora-3a,4a-diaza-s-indacene-3-propionic acid, BODIPY 493/503 (trade name): 4,4-difluoro-1,3,5,7-tetramethyl-4-bora-3a, 4a-diaza-s-indacene-8-propionic acid, BODIPY R6G (trade name): 4,4-difluoro-5-(4-phenyl-1,3-butadienyl)-4-bora-3a,4a-diaza-s-indacene-3-propionic acid, BODIPY 558/568 (trade name): 4,4-difluoro-5-(2-thienyl)-4-bora-3a,4a-diaza-s-indacene-3-propionic acid, BODIPY 564/570 (trade name): 4,4-difluoro-5-styryl-4-bora-3a,4a-diaza-s-indacene-3-propionic acid, BODIPY 576/589 (trade name): 4,4-difluoro-5-(2-pyrolyl)-4-bora-3a,4a-diaza-s-indacene-3-propionic acid, BODIPY 581/591 (trade name): 4,4-difluoro-5-(4-phenyl-1,3-butadienyl)-4-bora-3a,4a-diaza-s-indacene-3-propionic acid, EvoBlue10 (trade name), EvoBlue30 (trade name), MR121, ATTO 655 (trade name), ATTO 680 (trade name), ATTO 700 (trade name), ATTO MB2 (trade name), Alexa Fluor 350 (trade name), Alexa Fluor 405 (trade name), Alexa Fluor 430 (trade name), Alexa Fluor 488 (trade name), Alexa Fluor 532 (trade name), Alexa Fluor 546 (trade name), Alexa Fluor 555 (trade name), Alexa Fluor 568 (trade name), Alexa Fluor 594 (trade name), Alexa Fluor 633 (trade name), Alexa Fluor 680 (trade name), Alexa Fluor 700 (trade name), Alexa Fluor 750 (trade name), Alexa Fluor 790 (trade name), Flamma 496 (trade name), Flamma 507 (trade name), Flamma 530 (trade name), Flamma 552 (trade name), Flamma 560 (trade name), Flamma 575 (trade name), Flamma 581 (trade name), Flamma 648 (trade name), Flamma 675 (trade name), Flamma 749 (trade name), Flamma 774 (trade name), Flamma 775 (trade name), Rhodamine Red-X (trade name), Texas Red-X (trade name), 5(6)-TAMRA-X (trade name), STAMRA (trade name), Indocyanine green (ICG), and 2-((E)-2-((E)-2-(4-(2-carboxyethyl)phenoxy)-3-((E)-2-(3,3-dimethyl-5-sulfonato-1-(3-(tri-methyl ammonio)-propyl)indolin-2-ylidene)ethylidene)cyclohex-1-enyl)vinyl)-3,3-dimethyl-1-(3-(trimethyl ammonio)-propyl)-3H-indolium-5-sulfonate disodium bromide (ZW800-1). ATTO655 has a formula

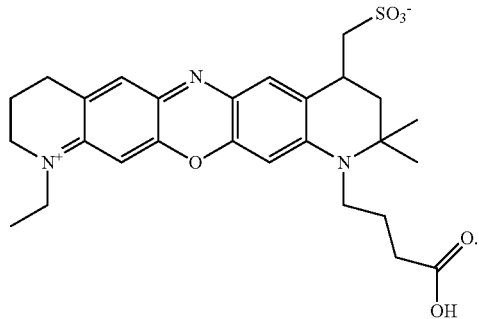

ATTO680 has a formula

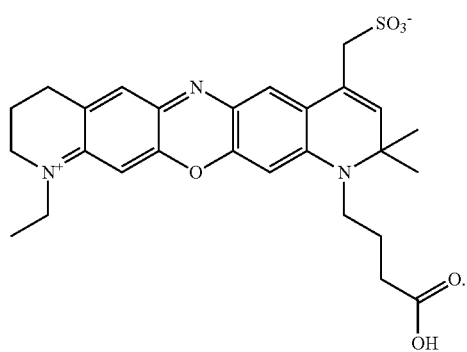

ATTO700 has a forumla

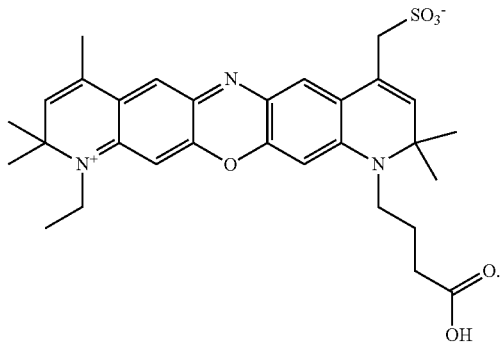

ATTO-MB2 has a formula

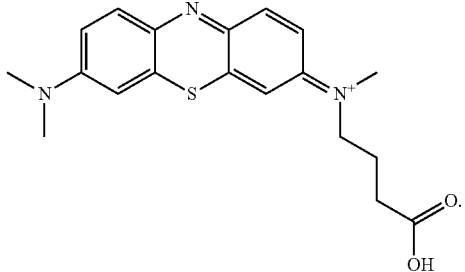 [SMILES: CN(C)c1ccc2nc3cc/c(=[N+](\C)CCCC(=O)O)cc-3sc2c1]

ZW800-1 has formula

In addition, the present invention provides an imaging kit for a cell, a tissue, and a tissue section, the kit comprising, as an active ingredient, the antibody-fluorescent dye conjugate according to the present invention.

In addition, the present invention provides a composition for diagnosing or detecting cancer through fluorescence imaging, the composition comprising, as an active ingredient, the antibody-fluorescent dye conjugate according to the present invention.

In an embodiment of the present invention, the composition may be a formulation for injection or a formulation for spraying.

Furthermore, the present invention provides a method for providing information for cancer detection or diagnosis through fluorescence imaging, the method comprising a step of treating a sample with the antibody-fluorescent dye conjugate according to the present invention to obtain a fluorescent signal image.

In order to achieve the above object, the present invention provides an antigen responsive antibody-fluorescent dye conjugate in which the antibody used for the antigen responsive antibody-fluorescent dye contains at least one tryptophan (or tyrosine), and the fluorescent dye which is bound to the antibody causes a quenching phenomenon due to interaction with a tryptophan (or tyrosine) residue so that fluorescence emittance is suppressed. In a case where a distance between the fluorescent dye which is bound to the antibody and tryptophan (or tyrosine) is within 1.5 nanometers, fluorescence is quenched due to a photo-induced electron transfer (PET) phenomenon. On the other hand, in a case where the antibody specifically binds to an antigen present on a cell surface, a distance between the fluorescent dye and the tryptophan (or tyrosine) residue becomes long from each other due to a three-dimensional conformational change of the antibody, and a quenching effect disappears, so that a strong fluorescent signal is emitted from the fluorescent dye. According to this principle, the antigen responsive antibody-fluorescent dye conjugate is quenched in a case of being located in a space outside a target cell, and emits a strong fluorescent signal in a case where the antibody-fluorescent dye conjugate is bound to a target antigen (or receptor) present on a surface of a cancer cell, which makes it possible to detect only a targeted cancer cell in real-time from a fluorescent image without performing a washing process.

The antigen to which the antibody-fluorescent dye conjugate according to the present invention specifically binds may be an antigen which is overexpressed on a surface of a tumor-associated cell or a specific normal cell.

The antigen responsive antibody-fluorescent dye conjugate according to the present invention is configured such that fluorescence emittance is suppressed in a case of being present in an extracellular region, and a quenching phenomenon disappears immediately upon binding to a targeted antigen and a strong fluorescent signal can be emitted. Thus, it is possible to perform detection and imaging diagnosis of a targeted cancer cell in in vivo and ex vivo tests in a very effective manner. Therefore, in a study or screening using cancer cells, it is possible to image and detect targeted cancer cells in real-time within a short time without performing a washing process. Even in a fluorescent image-guided cancer surgery, it is contemplated that locations of cancer cells or cancer tissues are detected with high contrast within a few hours to 24 hours after intravenous administration of the antibody-fluorescent dye conjugate, so that accuracy of the surgery and therapeutic efficiency for cancer can be dramatically enhanced.

BRIEF DESCRIPTION OF DRAWINGS

FIG. 9A is data obtained by intravenously administering the Trastuzumab-ATTO 680 conjugate at a concentration of 50 ug/50 ul to HER2-negative MDA-MB-231 tumor-xenografted mice and HER2-positive Calu-3 tumor-xenografted mice, respectively, and then obtaining near-infrared fluorescent images after 1 hour, 5 hours, and 24 hours in Example 1 according to the present invention. For a control, data obtained by administering phosphate buffered saline (PBS) to normal mice and obtaining images are shown. In the Calu-3 tumor-xenografted mice, a location of a tumor can be clearly distinguished from the fluorescent image with high contrast.

FIG. 10C is a result obtained by comparing fluorescence spectra for ATTO 680 the Cetuximab-ATTO 680 and the denatured Cetuximab-ATTO 680 at a concentration of 1 Um in Example 2 according to the present invention.

FIG. 11A is a result obtained by treating MCF7, which is EGFR-negative cancer cells, with the Cetuximab-ATTO 680 conjugate at a concentration of 10 ug/mL for 30 minutes, 1 hour, and 2 hours, respectively, performing washing, and then observing fluorescent images in Example 2 according to the present invention. In the MCF7 cells, even in a case of being treated with the Cetuximab-ATTO 680 conjugate for 2 hours, the antibody did not bind to cell surfaces.

FIG. 12 is fluorescent image data obtained by treating MDA-MB-468, which is EFGR-positive cancer cells, with the Cetuximab-ATTO 680 conjugate at a concentration of 10 ug/mL for 30 minutes, removing the antibody conjugate through washing, and making an observation after 30 minutes, 1 hour, 5 hours, and 24 hours in Example 2 according to the present invention.

DETAILED DESCRIPTION

Figure 1:
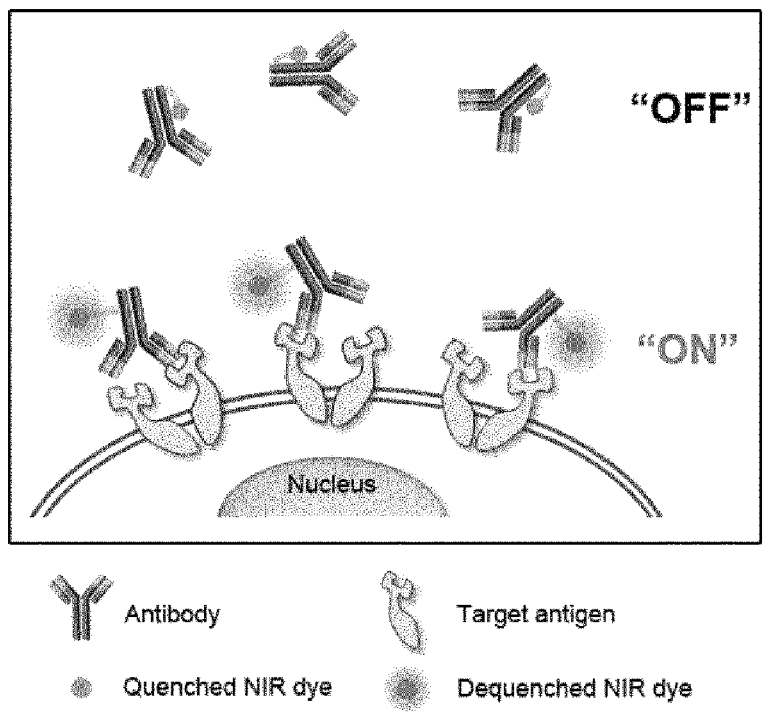
FIG. 1 is a schematic diagram for an action mechanism of the antigen responsive antibody-fluorescent dye conjugate according to the present invention. In a case where the antigen responsive antibody-fluorescent dye conjugate is present in an extracellular region, no fluorescent signal is emitted (turned OFF). Immediately upon binding of the conjugate to an antigen present on a surface of a cancer cell, the fluorescent dye which is bound to the antibody is allowed to emit a strong fluorescent signal (turned ON).
Figure 2A:
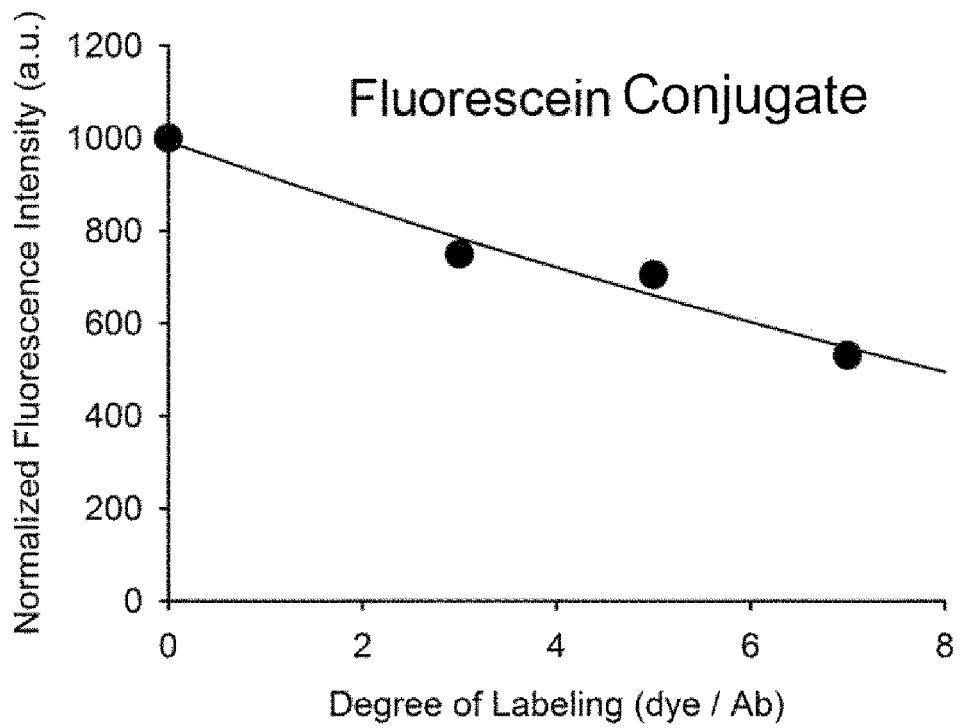
FIG. 2A is a result showing suppression of a fluorescence intensity with a degree of labeling in the Trastuzumab-Fluorescein conjugate of Example 1 according to the present invention ($\lambda$ex. 494 nm, $\lambda$em. 518 nm).
Figure 2B:
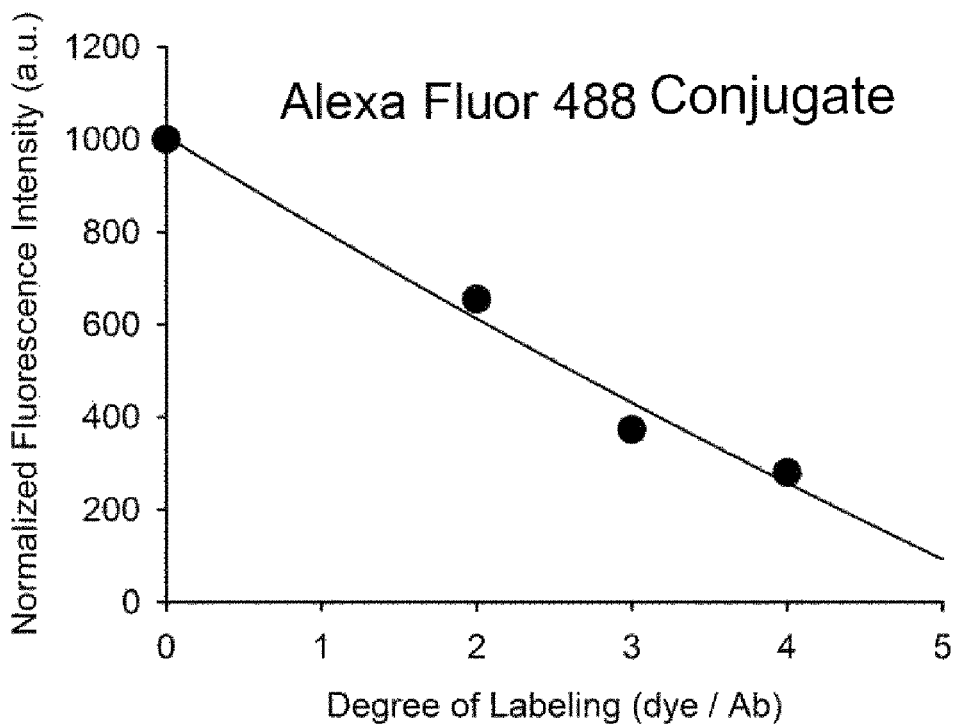
FIG. 2B is a result showing suppression of a fluorescence intensity with a degree of labeling in the Trastuzumab-Alexa Fluor®488 conjugate of Example 1 according to the present invention ($\lambda$ex. 495 nm, $\lambda$em. 519 nm).
Figure 2C:
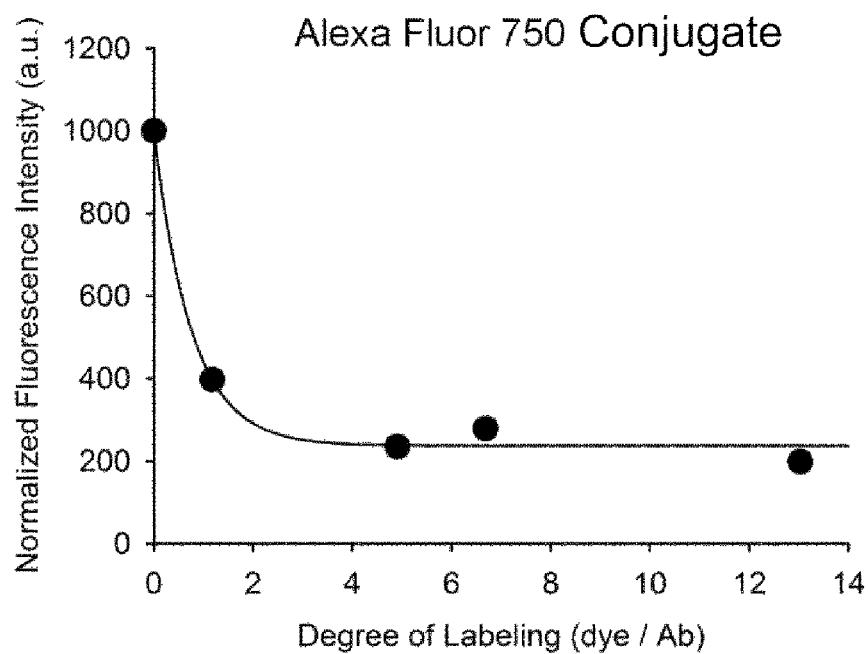
FIG. 2C is a result showing suppression of a fluorescence intensity with a degree of labeling in the Trastuzumab-Alexa Fluro®750 conjugate of Example 1 according to the present invention ($\lambda$ex. 753 nm, $\lambda$em. 782 nm).
Figure 2D:
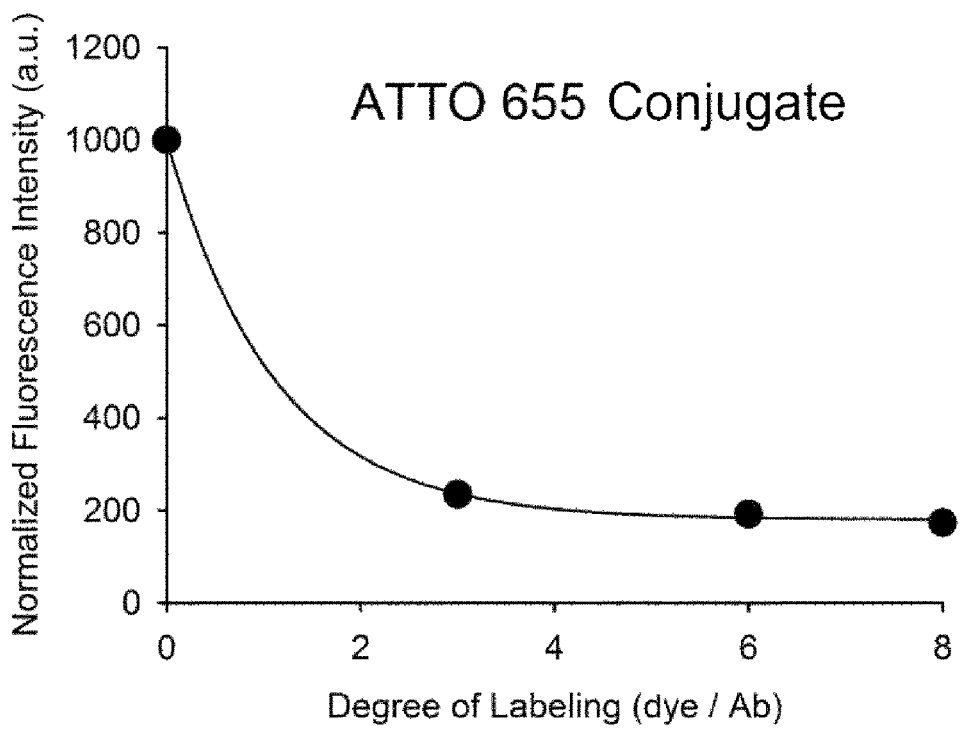
FIG. 2D is a result showing suppression of a fluorescence intensity with a degree of labeling in the Trastuzumab-ATTO 655 conjugate of Example 1 according to the present invention ($\lambda$ex. 663 nm, $\lambda$em. 684 nm).
Figure 2E:
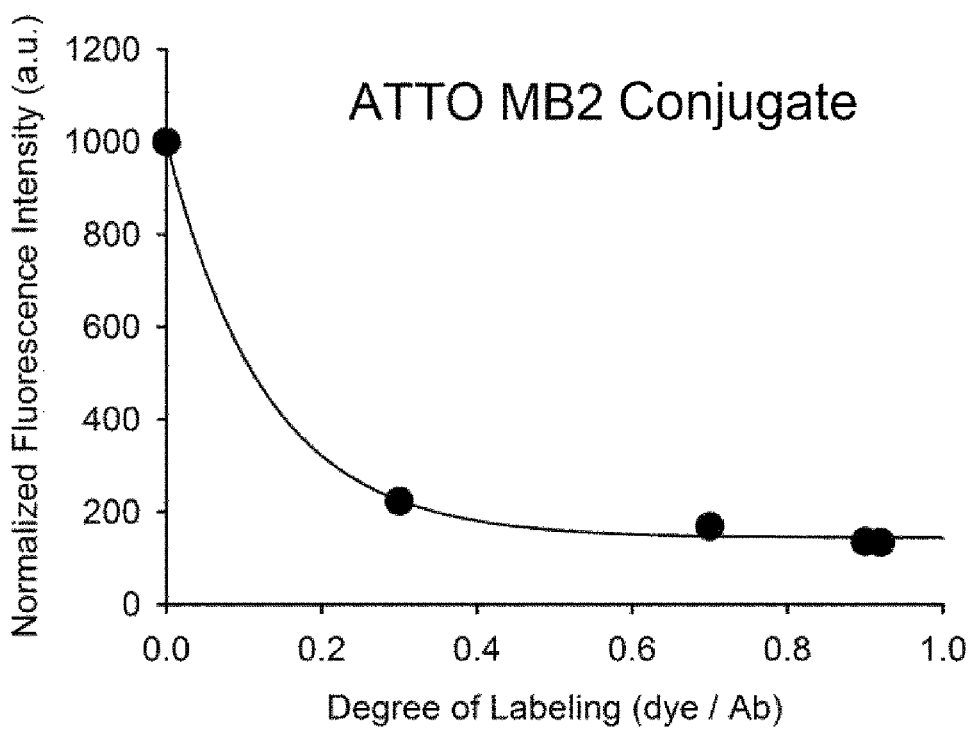
FIG. 2E is a result showing suppression of a fluorescence intensity with a degree of labeling in the Trastuzumab-ATTO MB2 conjugate of Example 1 according to the present invention ($\lambda$ex. 658 nm, $\lambda$em. 680 nm).
Figure 2F:
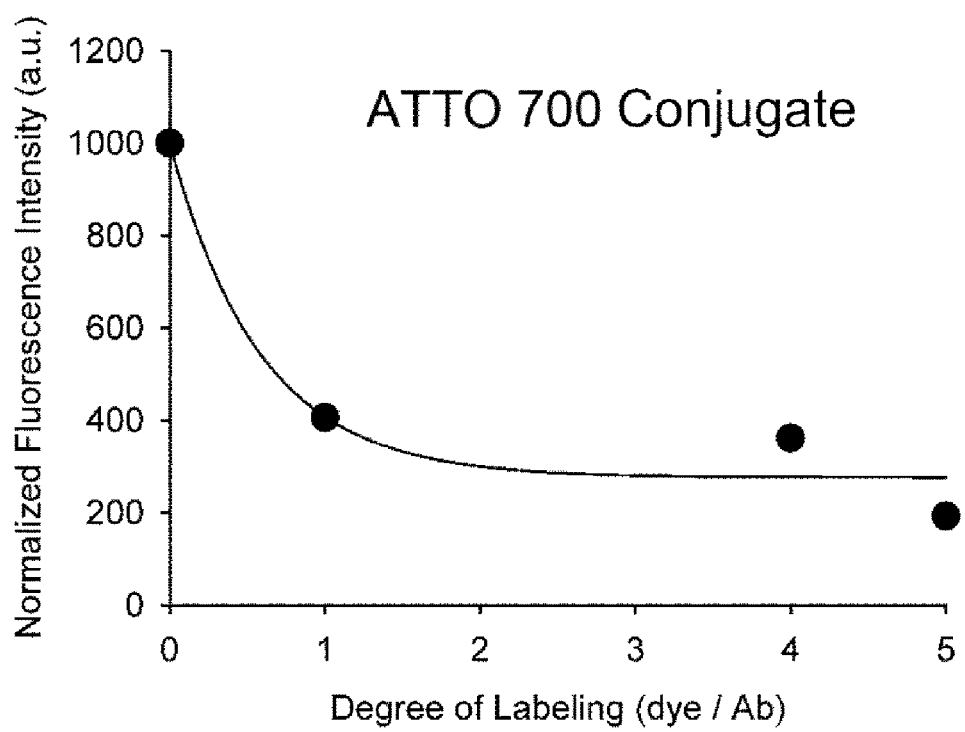
FIG. 2F is a result showing suppression of a fluorescence intensity with a degree of labeling in the Trastuzumab-ATTO 700 conjugate of Example 1 according to the present invention ($\lambda$ex. 700 nm, $\lambda$em. 719 nm).
Figure 2G:
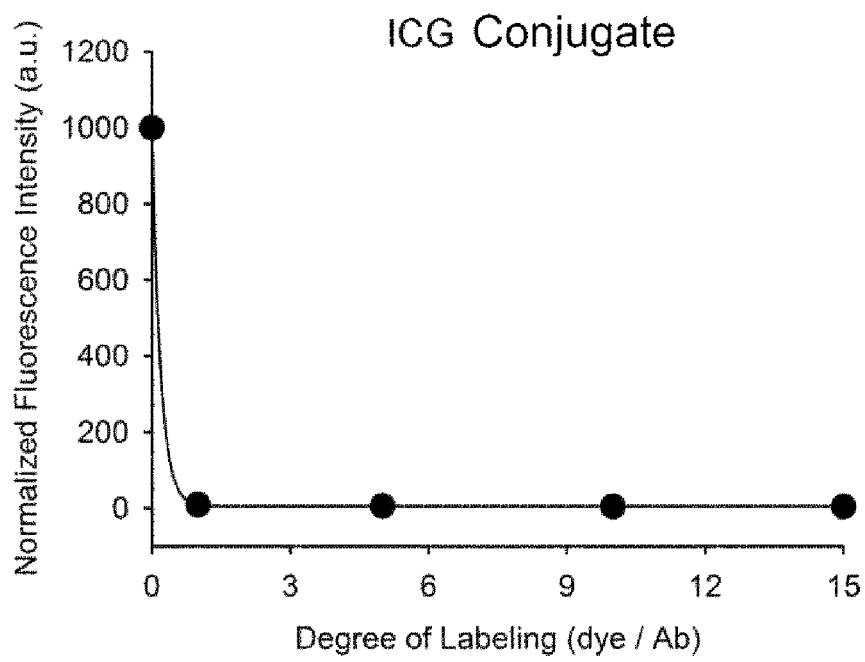
FIG. 2G is a result showing suppression of a fluorescence intensity with a degree of labeling in the Trastuzumab-ICG conjugate of Example 1 according to the present invention ($\lambda$ex. 790 nm, $\lambda$em. 800 nm).
Figure 2H:
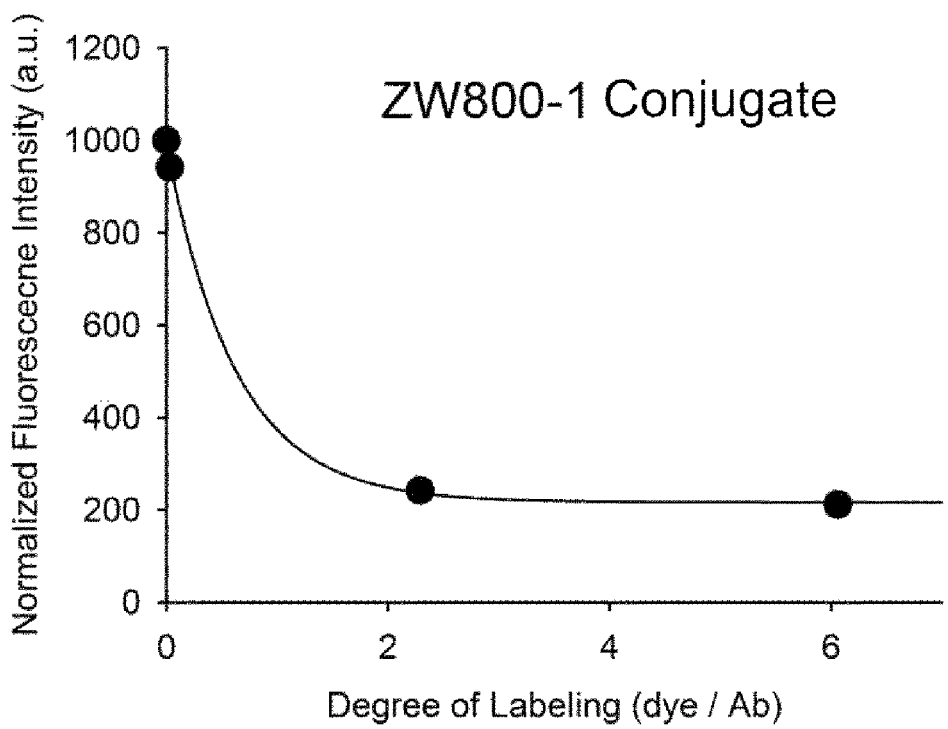
FIG. 2H is a result showing suppression of a fluorescence intensity with a degree of labeling in the Trastuzumab-ZW800-1 conjugate of Example 1 according to the present invention ($\lambda$ex. 770 nm, $\lambda$em. 788 nm).

In order to achieve the aforementioned objects, the present invention provides an antibody-fluorescent dye conjugate characterized by comprising an antibody labeled with a fluorescent dye, in which the fluorescent dye is quenched by interaction with a tryptophan (or tyrosine) residue which is an amino acid in the antibody, and is dequenched in a case where a three-dimensional structural change occurs upon antibody-antigen binding, and a method for imaging and diagnosing cancer cells using the same. In the fluorescent dye, a quenching effect is most effectively caused by tryptophan present in the antibody. However, the quenching effect can be obtained by interaction with a tyrosine, histidine, or methionine residue present in the antibody, and the quenching effect can be, in part, obtained even by aggregation among the fluorescent dyes. According to literature, it is known that in a case where tryptophan, tyrosine, histidine, and methionine are dissolved together with increasing concentrations thereof in an aqueous solution in which fluorescent dyes are dissolved, photo-induced electron transfer occurs between the amino acids and the fluorescent dyes so that the fluorescent dyes are quenched. Hereinafter, the present invention will be described in detail with reference to the drawings.

The present invention provides an antibody-fluorescent dye conjugate characterized by comprising an antibody labeled with a fluorescent dye, in which the fluorescent dye is quenched by interaction with a tryptophan (or tyrosine, histidine, or methionine) residue in the antibody, and is dequenched in a case where a three-dimensional structural change in the antibody occurs upon antibody-antigen binding so that a distance between the fluorescent dye and tryptophan (or tyrosine, histidine, or methionine) becomes long from each other and distances among the fluorescent dyes also become long from one another. The antibody used in the present invention is not limited to a specific type, and is characterized by including one or more tryptophan residues or a mixture of two or more tryptophan/tyrosine/histidine/methionine residues so that a quenching effect in the fluorescent dye which is bound to the antibody can be induced, and by binding to an antigen (or receptor) present on a cell membrane surface of a cancer cell. In order to effectively realize the fluorescence-quenching characteristic, it is preferable that tryptophan (or tyrosine, histidine, or methionine) is well preserved in an antibody molecule so that a quenching effect in the fluorescent dye can be obtained, and a lysine or cysteine residue for binding with the fluorescent dye is contained in the antibody. However, as known in the related art, it is also possible to perform labeling with the fluorescent dye after modification reaction of other amino acids present in the antibody. In the antigen responsive antibody-fluorescent dye conjugate, it is preferable that the lysine or cysteine residue for binding with the fluorescent dye is present in a constant region of a light chain or a heavy chain in the antibody, and antibodies characterized in that tryptophan (or tyrosine, histidine, or methionine) is present at a distance within 1.5 nanometers from a location at which the fluorescent dye is bound are preferred.

The fluorescent dye in the antibody-fluorescent dye conjugate according to the present invention may be labeled at an appropriate location to have the above-mentioned characteristics and to exert functions, and the number of the fluorescent dyes which covalently label the antibody is preferably one or more and may not exceed ten.

The antibody-fluorescent dye conjugate according to the present invention can be prepared by using a known chemical synthesis method, a gene recombination technique, a method of degrading an antibody molecule by a proteolytic enzyme, and the like. Among them, the gene recombination technique that allows preparation in a relatively easy manipulation and also in a large quantity is preferably used for preparation. In a case where an antibody having an amino acid sequence that has the above characteristics is prepared by the gene recombination technique, a DNA comprising a base sequence that encodes such an amino acid sequence is introduced into a suitable expression vector to produce a recombinant vector, and an antibody having a desired amino acid sequence is allowed to be expressed by an expression system using a bacterial cell, a yeast cell, an insect cell, an animal or plant cell, or the like as a host, or a cell-free translation system. In addition, for the antibody for producing the antibody-fluorescent dye conjugate, the above-mentioned conventional product may be obtained and used by synthesis using a conventional method. For example, it is possible to cause Trastuzumab (Herceptin) that specifically recognizes human epidermal growth factor receptor 2 (HER2) to be bound to a fluorescent dye, and to use the conjugate.

In the present invention, a method of performing labeling with a fluorescent dye is not particularly limited. A method of performing labeling, directly or via a cross-linking agent, using a side chain of a lysine or a cysteine residue present in a heavy chain and a light chain of the antibody can be used, but not limited thereto. Labeling with the fluorescent dye can be performed after modification reaction of other amino acids.

The antigen capable of being detected or measured by the antibody-fluorescent dye conjugate according to the present invention is not particularly limited as long as the antigen is an antigen which is specifically recognized by the antibody. Examples thereof include, in addition to proteins, peptides, saccharide, lipid, glycolipid, and low-molecular compounds, protein modifications such as phosphorylation and methylation, and proteins that have gone through these modifications. For example, the antigens associated with cancer cells to which the antibody-fluorescent dye conjugate according to the present invention specifically binds are characterized by including epidermal growth factor receptor (EGFR, HER1), human epidermal growth factor receptor 2 (HER2), human epidermal growth factor receptor 3 (HER3, ERBB-3), human epidermal growth factor receptor 4 (HER4, ERBB-4), epithelial cell adhesion molecule (EpCam), CD19, CD20, CD22 (Siglec-2), CD30 (TNFRSF1), CD33 (Siglec-3), CD44, CD44v6, CD52, CD56 (NCAM), CD152 (CTLA4), mucin 1 (MUC1), carcinoembryonic antigen (CEA), LEWIS Y, prostate-specific membrane antigen (PSMA), tumor-associated glycoprotein 72 (TAG-72), GD2 ganglioside, GD3 ganglioside, human leukocyte antigen-DR10 (HLA-DR10), insulin-like growth factor 1 receptor (IGF1R), tumor-associated antigen L6 (TAL6), tumor-necrosis factor-related apoptosis-inducing ligand receptor 2 (TRAILR2), vascular endothelial growth factor (VEGF), vascular endothelial growth factor receptor 2 (VEGFR2), platelet-derived growth factor receptor alpha (PDFGRA), hepatocyte growth factor receptor (HGFR), Alpha-v beta-3, Folate receptor, EGF-like domain-containing protein 7 (EGFL7), Fibroblast activation protein alpha (FAP), Carbonic anhydrase 9 (CA9/CAIX), and Vimentin.

As the antibody in the present invention, various antibodies targeting the above antigens can be used. For example, examples of monoclonal antibodies developed for clinical use include Cetuximab (Erbitux), Panitumumab (Vectibix), Necitumumab (Portrazza), Imgatuzumab, Matuzumab, Nimotuzumab, Futuximab, and Zalutumumab which are antibodies to an EGFR antigen, Trastuzumab (Herceptin) and Pertuzumab (Perjeta) which are antibodies to a HER2 antigen, Duligotumab, Patritumab, and Seribantumab which are antibodies to a HER3 antigen, Bevacizumab (Avastin) which is an antibody to a VEGF-A antigen, Catumaxomab (Removab) and Adecatumumab (MT201) which are antibodies to an EpCam antigen, Cixutumumab (IMC-A12), Figitumumab, Ganitumab, Robatumuma, Teprotumumab, and Dalotuzumab which are antibodies to an IGF1R antigen, Conatumumab (AMG 655), Drozitumab, Lexatumumab, and Tigatuzumab which are antibodies to a TRAILR2 antigen, Rituximab (Rituxan), Ibritumomab tiuxetan (Zevalin), Tositumomab (Bexxar), Ofatumumab (Arzerra), Ocaratuzumab, Ublituximab, and Obinutuzumab which are antibodies to a CD20 antigen, Epratuzumab (LymphoCide), Inotuzumab, and Narnatumab which are antibodies to a CD22 antigen, Brentuximab and Iratumumab which are antibodies to a CD30 antigen, Gentuzumab (Mylotarg) and Lintuzumab which are antibodies to a CD33 antigen, Bivatuzumab which is an antibody to a CD44v6 antigen, Alemtuzumab (Campath) which is an antibody to a CD52 antigen, Dinutuximab (Unituxin) which is an antibody to a GD2 ganglioside antigen, and Ecromeximab which is an antibody to a GD3 ganglioside antigen. Other antibodies include Olaratumab which is an antibody to a platelet-derived growth factor receptor alpha (PDFGRA) antigen, Emibetuzumab which is an antibody to a hepatocyte growth factor receptor (HGFR) antigen, Etaracizumab (Abegrin) which is an antibody to an Alpha-v beta-3 antigen, Farletuzumab which is an antibody to a Folate receptor alpha antigen, Parsatuzumab which is an antibody to an EGF-like domain-containing protein 7 (EGFL7) antigen, Sibrotuzumab which is an antibody to a Fibroblast activation protein alpha (FAP) antigen, and Girentuximab (Rencarex) which is an antibody to a Carbonic anhydrase 9 (CA9/CAIX) antigen.

In the present invention, the fluorescent dye used for antibody labeling is not particularly limited as long as the fluorescent dye is a fluorescent dye which has a characteristic of being effectively quenched in a case of being located at a distance within 1.5 nm from tryptophan, tyrosine, methionine, or histidine, and which is quenched, in a state of forming a conjugate with an antibody and in the absence of an antigen, by interaction with the above-mentioned amino acids, more specifically by a photo-induced electron transfer mechanism, and is dequenched to restore fluorescence emittance in a case where the antibody-fluorescent dye conjugate is bound to an antigen. As the fluorescent dye used for fluorescence labeling, fluorescent dyes having, as a basic skeleton, rhodamine, coumarin, EvoBlue, oxazine, carbopyronine, naphthalene, biphenyl, anthracene, phenanthrene, pyrene, carbazole, or the like, and derivatives of the fluorescent dyes may be exemplified, and specific examples thereof include Fluorescein, CR110: Carboxyrhodamine 110: Rhodamine Green (trade name), TAMRA: carboxytetramethylrhodamine: TMR, Carboxyrhodamine 6G: CR6G, BODIPY FL (trade name): 4,4-difluoro-5,7-dimethyl-4-bora-3a,4a-diaza-s-indacene-3-propionic acid, BODIPY 493/503 (trade name): 4,4-difluoro-1,3,5,7-tetramethyl-4-bora-3a, 4a-diaza-s-indacene-8-propionic acid, BODIPY R6G (trade name): 4,4-difluoro-5-(4-phenyl-1,3-butadienyl)-4-bora-3a,4a-diaza-s-indacene-3-propionic acid, BODIPY 558/568 (trade name): 4,4-difluoro-5-(2-thienyl)-4-bora-3a,4a-diaza-s-indacene-3-propionic acid, BODIPY 564/570 (trade name): 4,4-difluoro-5-styryl-4-bora-3a,4a-diaza-s-indacene-3-propionic acid, BODIPY 576/589 (trade name): 4,4-difluoro-5-(2-pyrolyl)-4-bora-3a,4a-diaza-s-indacene-3-propionic acid, BODIPY 581/591 (trade name): 4,4-difluoro-5-(4-phenyl-1,3-butadienyl)-4-bora-3a,4a-diaza-s-indacene-3-propionic acid, EvoBlue10 (trade name), EvoBlue30 (trade name), MR121, ATTO 655 (trade name), ATTO 680 (trade name), ATTO 700 (trade name), ATTO MB2 (trade name), Alexa Fluor 350 (trade name), Alexa Fluor 405 (trade name), Alexa Fluor 430 (trade name), Alexa Fluor 488 (trade name), Alexa Fluor 532 (trade name), Alexa Fluor 546 (trade name), Alexa Fluor 555 (trade name), Alexa Fluor 568 (trade name), Alexa Fluor 594 (trade name), Alexa Fluor 633 (trade name), Alexa Fluor 680 (trade name), Alexa Fluor 700 (trade name), Alexa Fluor 750 (trade name), Alexa Fluor 790 (trade name), Flamma 496 (trade name), Flamma 507 (trade name), Flamma 530 (trade name), Flamma 552 (trade name), Flamma 560 (trade name), Flamma 575 (trade name), Flamma 581 (trade name), Flamma 648 (trade name), Flamma 675 (trade name), Flamma 749 (trade name), Flamma 774 (trade name), Flamma 775 (trade name), Rhodamine Red-X (trade name), Texas Red-X (trade name), 5(6)-TAMRA-X (trade name), STAMRA (trade name), Indocyanine green (ICG), and 2-((E)-2-((E)-2-(4-(2-carboxyethyflphenoxy)-3-((E)-2-(3,3-dimethyl-5-sulfonato-1-(3-(tri-methyl ammonio)-propyl)indolin-2-ylidene)ethylidene)cyclohex-1-enyl)vinyl)-3,3-dimethyl-1-(3-(trimethyl ammonio)-propyl)-3H-indolium-5-sulfonate disodium bromide (ZW800-1).

Another aspect of the present invention provides a kit for imaging diagnosis of a tumor, the kit configured to comprise the aforementioned antibody-fluorescent dye conjugate and further comprise reagents or the like which are usually used in this type of immunoassay kit, instruments, instructions, and the like.

The present invention provides a method for fluorescence imaging and diagnosis, the method comprising a step (a) of bring an antibody-fluorescent dye conjugate into contact with an antigen in a sample, the antibody-fluorescent dye conjugate being characterized by comprising an antibody labeled with a fluorescent dye in which the fluorescent dye is quenched by interaction with a tryptophan or tyrosine residue in the antibody and is dequenched upon antibody-antigen binding; and a step (b) of obtaining fluorescence of the fluorescent dye as an image and performing analysis.

A method of bringing the antibody-fluorescent dye conjugate according to the present invention into contact with the antigen is not limited to a particular method, and may be performed in a liquid state or may be performed in vivo or ex vivo. A liquid-state specimen may be supplied, as it is, for measurement as a measurement sample, or may be used by dilution with a buffer solution or a cell culture medium, concentration, or proper adjustment of a pH, a salt concentration, or the like to the extent that the antigen is not damaged or detection for antigen concentration measurement is not inhibited.

The liquid-state specimen may be, for example, adherent or suspension cells to be measured, and diagnosis is performed through fluorescence imaging after treatment with the antibody-fluorescent dye conjugate.

In the present invention, body fluids such as blood and fluid, tissues, and the like in a living body can also be used as a sample to be measured. That is, the antibody-fluorescent dye conjugate of the present invention is administered to an experimental animal or a human so that the antibody-fluorescent dye conjugate of the present invention can be brought into contact with an antigen in a living body. The above administration method is not particularly limited, and can be appropriately selected from a parenteral local administration method such as intramuscular injection, intraperitoneal injection, intravenous injection, subcutaneous injection, embedding, application, and spraying, or an oral administration method. In addition, other drugs or the like may be administered simultaneously with, or before or after administration of the antibody-fluorescent dye conjugate of the present invention. Administration of the antibody-fluorescent dye conjugate of the present invention allows a location or migration of an antigen and an antigen amount or a change thereof in a living body to be shown from a fluorescent image and allows qualitative and quantitative analysis, which enables real-time identification of a location of a target cell during surgery and can dramatically enhance accuracy of surgery and therapeutic effects.

For ex vivo fluorescence imaging analysis, for example, a fluorescent image may be obtained by directly treating tissues or cells taken from a living body with a solution in which the antibody-fluorescent dye conjugate is dispersed, or a fluorescent image may be obtained by producing sections from the tissues or cells and treating the same with a solution in which the antibody-fluorescent dye conjugate is dispersed. In addition, presence or absence of a target antigen may be diagnosed by treating a tissue or cell microarray obtained from a living body with a solution in which the antibody-fluorescent dye conjugate is dispersed, and obtaining a fluorescent image.

A reaction condition for bringing the antibody-fluorescent dye conjugate of the present invention into contact with an antigen in a measurement sample is not particularly limited as long as the condition is such that the antibody-fluorescent dye conjugate of the present invention is added to the measurement sample and culturing is performed under a condition which can be generally used for antigen-antibody reaction. A fluorescent image can be obtained by setting a temperature condition to, for example, 1° C. to 40° C., and preferably 18° C. to 37° C., and setting a reaction time to, for example immediately to 180 minutes, and preferably 1 to 90 minutes. In addition, in a case of being administered into a human or animal body, after waiting for, for example, 5 minutes to 24 hours following administration, a fluorescent image is obtained by using fluorescence imaging equipment and analysis is performed.

A fluorescence imaging method for a measurement sample in the present invention is not particularly limited as long as the method can detect fluorescence emitted from the fluorescent dye, and it is sufficient that the method images and/or detects fluorescence emittance from the fluorescent dye by causing the measurement sample after reaction to be irradiated with excitation light. Wavelengths of the excitation light to be irradiated and the fluorescence to be measured and/or detected can be appropriately selected depending on a type of the fluorescent dye to be used. For example, in a case where ATTO 680 is used for the fluorescent dye, a combination of excitation light wavelength of 660 nm and fluorescence emission wavelength of 710 nm can be used.

Hereinafter, the present invention will be described in more detail with reference to examples. However, it should be understood that these examples are only for illustrating the present invention and are not to be construed as limiting the scope of the present invention.

EXAMPLES

Example 1

1.1. Synthesis of Trastuzumab-Fluorescent Dye Conjugate

Example 1 was intended to demonstrate a basic concept and utility of an antigen responsive antibody-fluorescent dye conjugate, by using an antibody that specifically binds to Human Epidermal Growth Factor Receptor 2 (HER2) which is known to be over-expressed on surfaces of cancer cells, and causing various fluorescent dyes to be bound thereto. In particular, various fluorescent dyes are caused to be bound to Trastuzumab (Herceptin), which is a representative antibody used in clinical practice among antibodies that specifically bind to HER2, and a fluorescence-quenching effect was analyzed. For synthesis of antibody-fluorescent dye conjugates, Trastuzumab (0.5 mg, 3.4 nmol), and each of amine-reactive fluorescent dyes NHS-Fluorescein, Alexa Fluor®488 NHS ester, Alexa Fluor®750-NHS ester, ATTO 655-NHS ester, ATTO 680-NHSO ester, ATTO 700-NHS ester, a methylene blue derivative ATTO MB2-NHS ester, Indocyanine green sulfo-NHS ester (ICG), and ZW800-1-NHS ester were dissolved together at various molar ratios (molar ratio of antibody:dye=1:1, 1:5, 1:10, and 1:15) in 0.3 mL of phosphate buffered saline (PBS, pH 7.4, 10 mM, NaCl 137 mM), and an antibody-fluorescent dye binding reaction was allowed to proceed while stirring at room temperature for 1 hour. After completion of the reaction, unbound fluorescent dyes and reaction byproducts were removed using a PD-10 column (GE Healthcare). After purification, the obtained Trastuzumab-fluorescent dye conjugates were concentrated using an Amicon Ultra-0.5 mL (cut off: 50 kDa) centrifugal filter and stored in a refrigerator at 4° C.

1.2. Analysis of Trastuzumab-Fluorescent Dye Conjugate (1) Analysis of Degree of Labeling and Quenching Characteristic of Conjugate In order to analyze a degree of labeling (DL) of the fluorescent which is dye bound to the antibody, the antibody conjugate was dissolved in phosphate buffered saline and a UV/Vis absorbance spectrum was measured. A concentration of the antibody was calculated using a molar absorbance coefficient (210,000 $M^{-1}$ $cm^{-1}$) of Trastuzumab at 280 nm. For the fluorescent dye, a degree of labeling of the fluorescent dye which is bound to the antibody was analyzed by using a known molar absorbance coefficient value for each dye.

In order to measure a degree of quenching of the resulting antibody-fluorescent dye conjugate, each of the Trastuzumab-fluorescent dye conjugates was dissolved to a concentration of 1 uM (based on a fluorescent dye concentration), a fluorescence intensity was measured, and decreased fluorescence intensity with a degree of labeling was analyzed. For comparison, fluorescence spectrum and fluorescence intensity for a free fluorescent dye, which is not bound to an antibody, at the same concentration were measured, and comparison with the antibody-fluorescent dye conjugates was performed.

In order to observe whether fluorescence is restored in a case where a three-dimensional structure of the antibody-fluorescent dye conjugate is changed, Trastuzumab-ATTO 680 conjugates (samples with a degree of labeling of 3.77) were treated with phosphate buffered saline and a denaturing buffer solution (phosphate buffered saline containing 1% sodium dodecyl sulfate (SDS) and 1 mM 2-mercaptoethanol), respectively, and absorbances and fluorescence spectra were compared ($\lambda$ex. 620 nm, $\lambda$em. 640 to 850 nm).

Figure 3A:
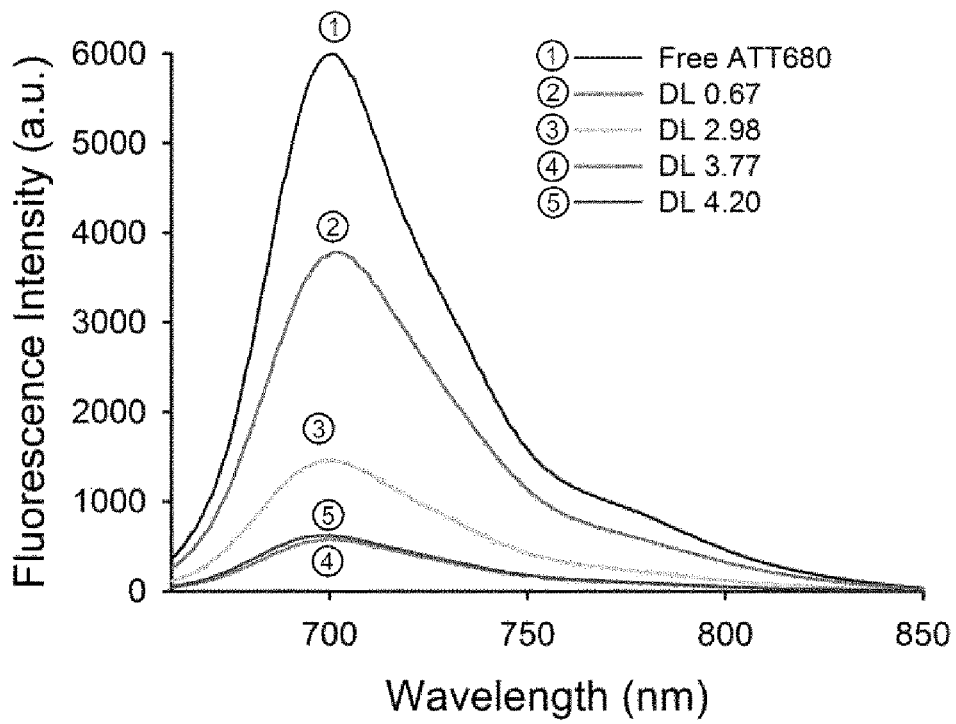
FIG. 3A is fluorescence spectrum ($\lambda$ex. 620 nm, $\lambda$em. 640 to 850 nm) data with a degree of labeling (DL) for the Trastuzumab-ATTO 680 conjugate of Example 1 according to the present invention. A fluorescence spectrum of ATTO 680, which is a free fluorescent dye, at the same concentration (1 uM) is shown for comparison.
Figure 3B:
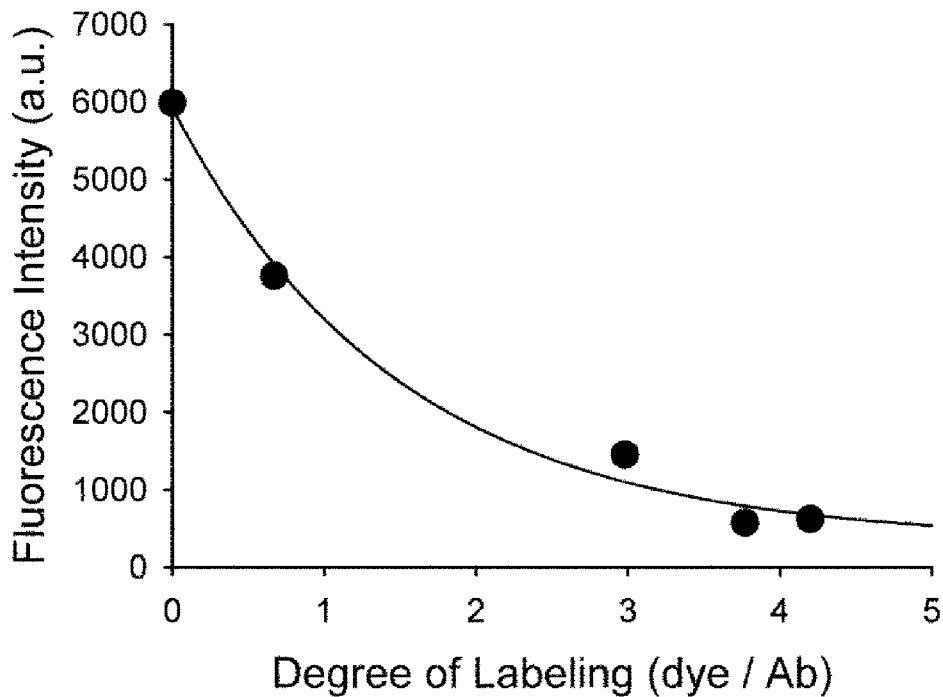
FIG. 3B is a result showing suppression of a fluorescence intensity with a degree of labeling in the Trastuzumab-ATTO 680 conjugate of Example 1 according to the present invention.
Figure 3C:
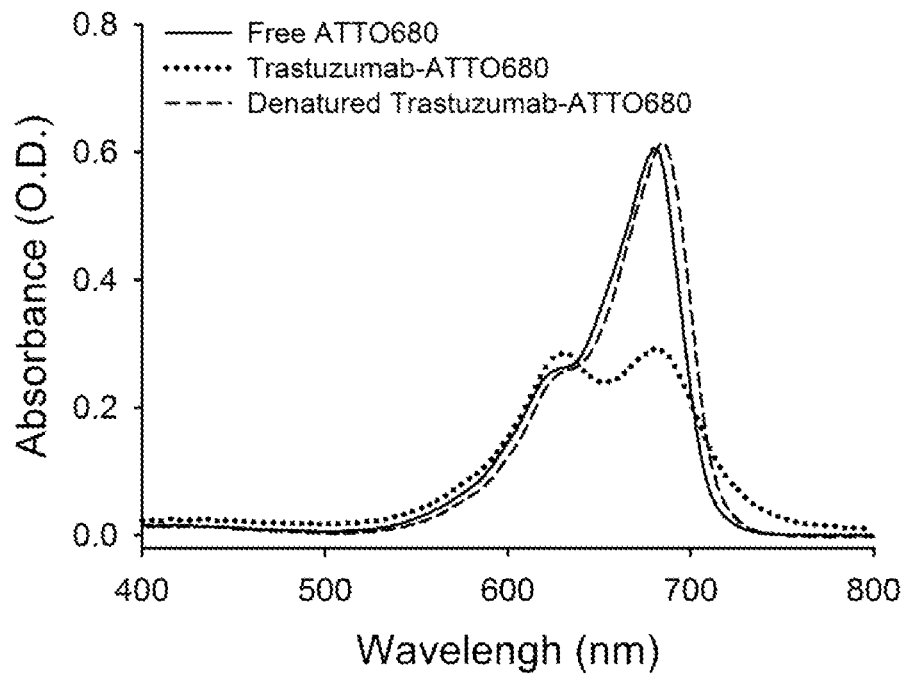
FIG. 3C is a result comparing absorbance spectra of ATTO 680, the Trastuzumab-ATTO 680 conjugate (sample with a degree of labeling of 3.77) and the denatured Trastuzumab-ATTO 680 conjugate (sample with a degree of labeling of 3.77), at a concentration of 5 uM, of Example 1 according to the present invention.

The analysis results for quenching characteristics of the synthesized Trastuzumab-fluorescent dye conjugates are shown in FIG. 2. A value at a degree of labeling of 0 is a fluorescence value for a free fluorescent dye at the same concentration. As can be seen in FIG. 2 and FIG. 3B, for all conjugates with various fluorescent dyes such as Fluorescein, Alexa Fluor®488, Alexa Fluor®750, ATTO 655, ATTO 700, ATTO MB2, ATTO 680 ICG, and ZW800-1, it was found that a quenching effect can be obtained even in a case where a degree of labeling is 1, which supports that an action mechanism for the quenching effect is due to photo-induced electron transfer between tryptophan (or tyrosine, histidine, or methionine) and the fluorescent dye. The quenching effect in the fluorescent dye was further increased as the degree of labeling was increased.

Figure 3D:
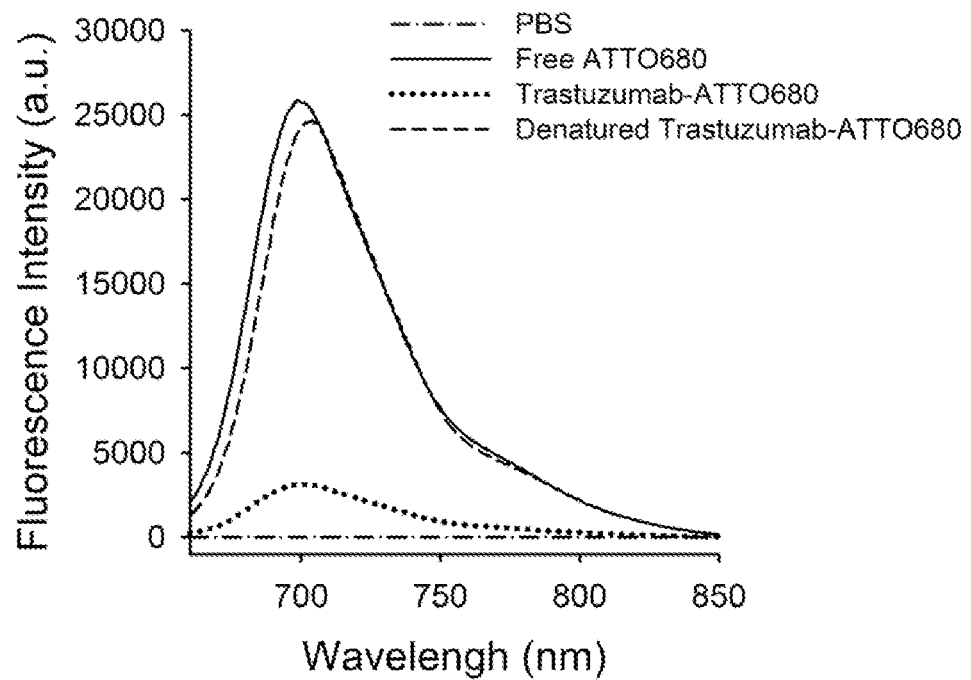
FIG. 3D is a result comparing absorbance spectra of ATTO 680, the Trastuzumab-ATTO 680 conjugate (sample with a degree of labeling of 3.77) and the denatured Trastuzumab-ATTO 680 conjugate (sample with a degree of labeling of 3.77), at a concentration of 1 uM, of Example 1 according to the present invention. For a control, a fluorescence spectrum for dye-free phosphate buffered saline (PBS) is shown.
Figure 3E:
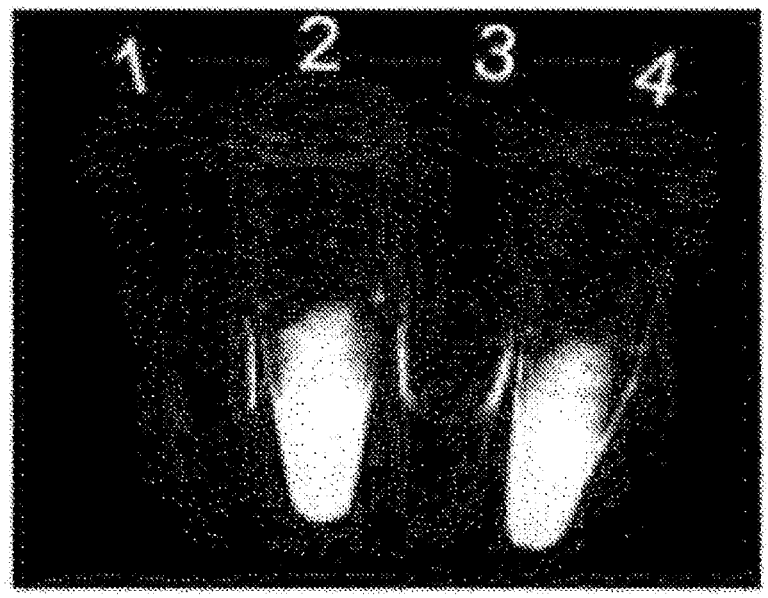
FIG. 3E is a result of near-infrared fluorescent image measurement for the Trastuzumab-ATTO 680 (sample with a degree of labeling of 3.77) of Example 1 according to the present invention ($\lambda$ex. 640/25 nm, $\lambda$em. 732/37 nm). 1: Phosphate buffered aqueous solution (PBS), 2: ATTO 680 dye, 3: Trastuzumab-ATTO 680 conjugate, 4: denatured Trastuzumab-ATTO 680 conjugate.

According to FIGS. 3D and 3E, in a case where an antibody is labeled with 3.77 ATTO 680 fluorescent dyes, it was analyzed that a fluorescent signal was 7.9 times weaker than a free fluorescent dye (free ATTO 680 control group) at the same concentration. In addition, it was found that in a case where the conjugate is treated with a denaturing buffer solution, fluorescence is restored to an original fluorescence intensity. FIG. 3E is a photograph of near-infrared fluorescent image ($\lambda$ex. 640/25 nm, $\lambda$em. 732/37 nm) taken using animal fluorescence imaging equipment to visually show quenching characteristic and fluorescence restoration of the antibody-fluorescent dye conjugate. It can be visually identified that a fluorescent dye (no. 2 tube in FIG. 3E) inherently capable of emitting strong fluorescence becomes quenched (no. 3 tube in FIG. 3E) after being bound to an antibody, and it can be seen in an intuitive way that fluorescence is restored again (no. 4 tube in FIG. 3E) in a case of being treated with a denaturing buffer solution so that interaction between the fluorescent dye and amino acids is removed. For comparison, a fluorescent image for phosphate buffered saline (PBS, no. 1 tube in FIG. 3E) containing no fluorescent dye is also shown, which shows that phosphate buffered saline itself does not emit fluorescence.

The subsequent cell and animal experiments were intended to demonstrate a basic concept and utility of the antigen responsive antibody-fluorescent dye conjugate, by proceeding with experiments using conjugates in which 3.77 ATTO 680's are bound to Trastuzumab.

(2) Analysis of Stability in Serum

It was analyzed whether the antigen responsive antibody-fluorescent dye conjugate stably retains a quenching effect therein even under a serum condition in which proteins are contained. For this purpose, the Trastuzumab-ATTO 680 conjugates (samples with a degree of labeling of 3.77) were dispersed in phosphate buffered saline and a serum solution, respectively, and changes in fluorescence intensity were measured for 24 hours.

Figure 4:
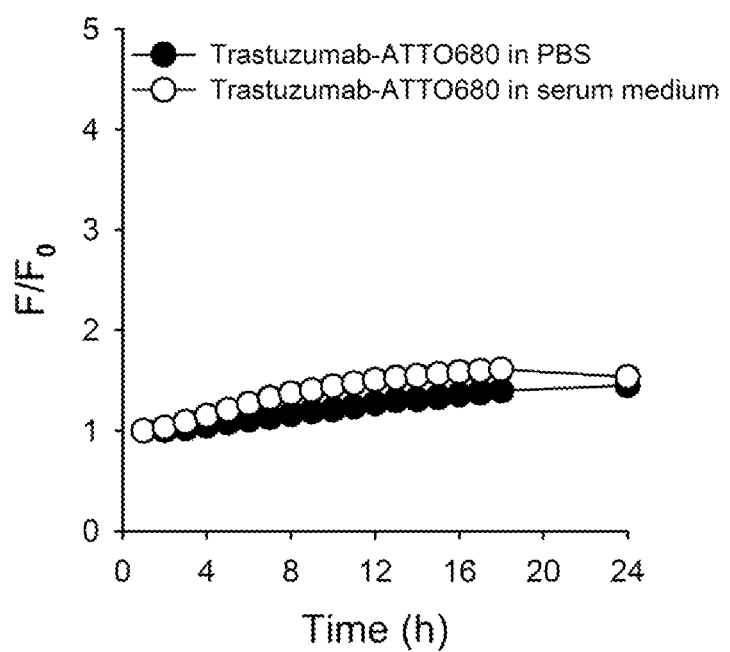
FIG. 4 is analysis data showing whether a fluorescence-quenching effect in the Trastuzumab-ATTO 680 (degree of labeling of 3.77), which is the antibody-fluorescent dye of Example 1 according to the present invention, is stably maintained under a serum condition. The conjugates were dispersed in a phosphate buffered saline and a serum culture medium, respectively, and changes in near-infrared fluorescence intensity with time were measured. In view of proportions of fluorescence (F) at the respective time points as compared with fluorescence ($F_0$) at 0 hours, it can be seen that a quenching state of the Trastuzumab-ATTO 680 conjugate is stably maintained even in the serum culture medium.

As a result of evaluation, it was found that the conjugate stably retains a quenched state for 24 hours under a serum condition (see FIG. 4), which means that the Trastuzumab-ATTO 680 conjugate restores fluorescence emittance and emits a strong fluorescent signal only in a case of being bound to an antigen (HER2).

(3) Analysis of Antigen Binding Specificity of Trastuzumab-ATTO 680 Conjugate

A cell experiment proceeded which identifies whether the antibody Trastuzumab retains binding specificity with the target antigen HER2 even after the antibody is bound to the fluorescent dye ATTO 680. For this purpose, HER2-negative cancer cell line MDA-MB-231, which does not express HER2, and HER2-positive cancer cell lines Calu-3 and SK-BR-3, which overexpress HER2, were purchased from ATCC, USA, and used. The MDA-MB-231 cancer cell line, and the SK-BR-3 and Calu-3 cancer cell lines were treated with the Trastuzumab-ATTO 680 at a concentration of 10 mg/mL for each of 30 minutes or 1 hour, respectively. Washing was performed to remove antibodies which are not bound to cells, and then fluorescent images were obtained using a confocal microscope to identify whether the antibody-fluorescent dye conjugate is bound to a surface of each cell ($\lambda$ex 633 nm, $\lambda$em 647 to 754 nm).

Figure 5A:
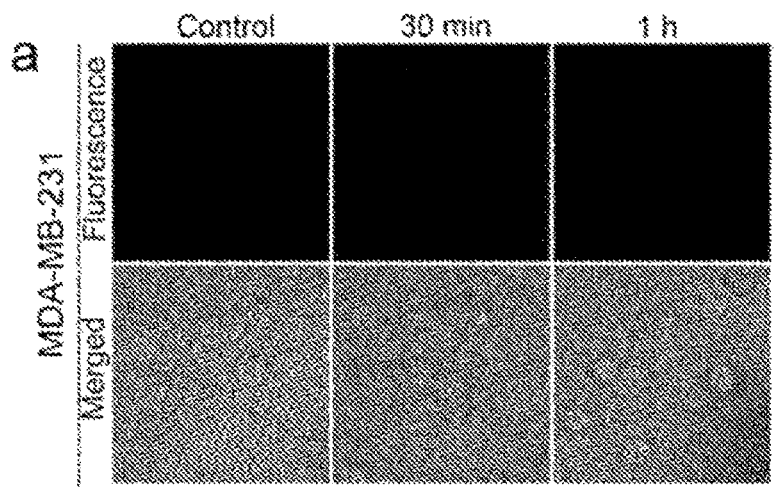
FIG. 5A is a result obtained by treating HER2-negative control cancer cells (MDA-MB-231) with the Trastuzumab-ATTO 680 conjugate at a concentration of 10 ug/mL for each of 30 minutes and 1 hour, performing washing, and then using a conformal microscope to acquire fluorescent images in Example 1 according to the present invention ($\lambda$ex. 633 nm, $\lambda$em. 647 to 754 nm).
Figure 5B:
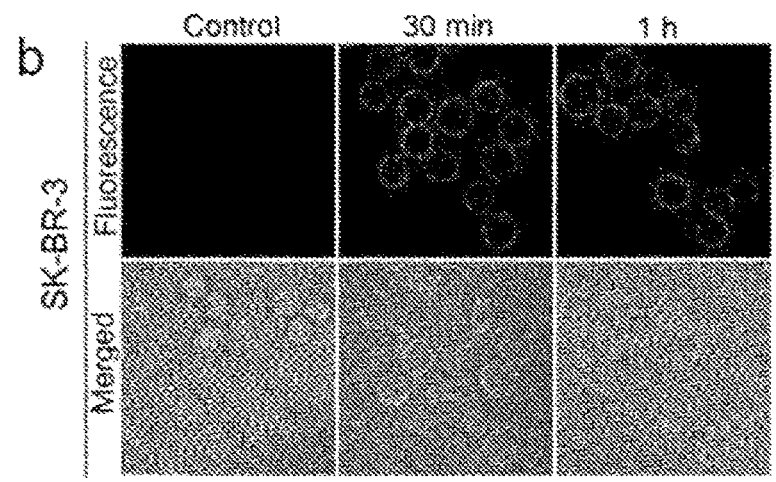
FIG. 5B is a result obtained by treating HER2-overexpressing cancer cells (SK-BR-3) with the Trastuzumab- ATTO 680 conjugate at a concentration of 10 ug/mL for each of 30 minutes and 1 hour, performing washing, and then using a conformal microscope to acquire fluorescent images in Example 1 according to the present invention (λex. 633 nm, λem. 647 to 754 nm).
Figure 5C:
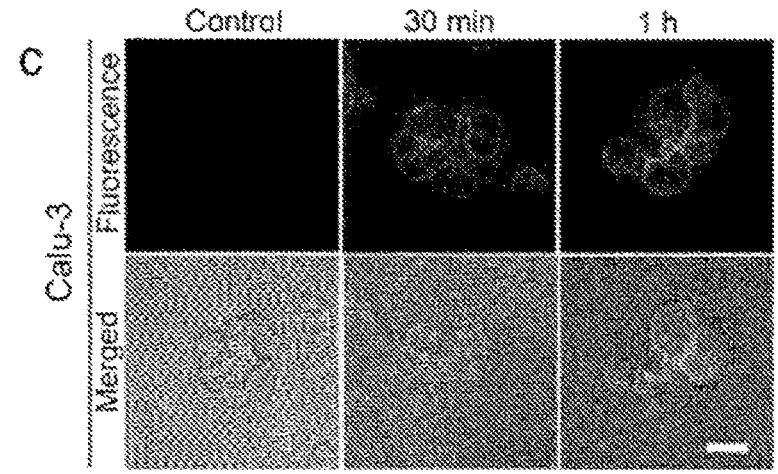
FIG. 5C is a result obtained by treating HER2-overexpressing cancer cells (Calu-3) with the Trastuzumab-ATTO 680 conjugate at a concentration of 10 ug/mL for each of 30 minutes and 1 hour, performing washing, and then using a conformal microscope to acquire fluorescent images in Example 1 according to the present invention (λex. 633 nm, λem. 647 to 754 nm).

According to the confocal microscopic data of FIG. 5, it can be seen that the Trastuzumab-ATTO 680 conjugate emits a strong fluorescent signal on a surface of the cancer cell overexpressing HER2, but no fluorescent signal could be detected on a surface of a MDA-MB-231 cell which is a HER2-negative cancer cell. From this, it can be seen that the Trastuzumab-ATTO 680 conjugate can be used to specifically image and diagnose a HER2-overexpressing cancer cell line.

(4) Characterization of Fluorescent Signal Activation by Interaction with Antigen A cell experiment was intended to verify whether a fluorescent signal in the antibody-fluorescent dye conjugate is turned on immediately upon reaction with an antigen present on a surface of a cancer cell. It was expected that the Trastuzumab-ATTO 680 conjugate does not emit a fluorescent signal in a case of being present on a cell culture medium, and is caused to activate fluorescence emittance and emit a strong fluorescent signal in a case of being bound to the target antigen HER2 present on a surface of a cancer cell. Therefore, the present example was intended to demonstrate a basic concept and utility of the antigen responsive antibody-fluorescent dye conjugate, by taking a fluorescent image every 1 minute without performing washing in a case of obtaining the fluorescent image after treating an antigen-overexpressing cancer cell line with the antibody-fluorescent dye conjugate. For this purpose, the HER2 overexpressing cancer cell SK-BR-3 was treated with the Trastuzumab-ATTO 680 conjugate at a concentration of 10 ug/mL, and then fluorescent images of the cancer cell were obtained using a confocal microscope every 1 minute without performing a washing process ($\lambda$ex. 633 nm, $\lambda$em. 647 to 754 nm). For comparison, the SK-BR-3 cancer cell was treated with a free fluorescent dye (free ATTO 680) at a concentration of 1 uM, and then confocal fluorescent images before and after performing washing were obtained.

Figure 6A:
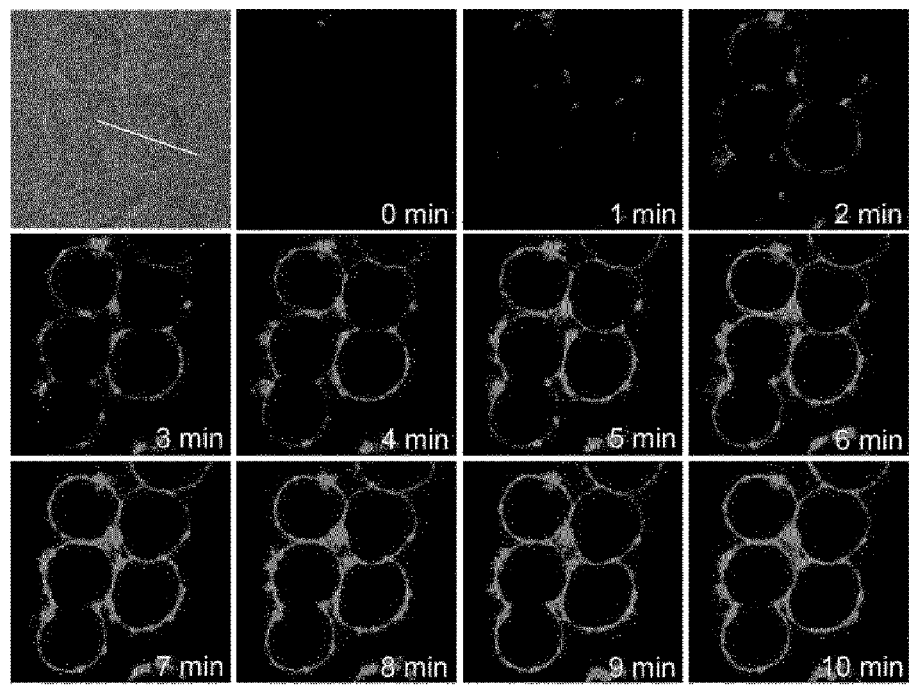
FIG. 6A is a result obtained by treating HER2-overexpressing cancer cells (SK-BR-3) with the Trastuzumab-ATTO 680 conjugate, and using a conformal microscope at a 1-minute interval, without a washing process, to acquire fluorescent images in Example 1 according to the present invention (λex. 633 nm, λem. 647 to 754 nm). The drawing shows that as the quenched Trastuzumab-ATTO 680 conjugate binds to a HER2 antigen on a cell membrane, a strong fluorescent signal is emitted on the cell membrane. In an extracellular region, a fluorescent signal is hardly detected because the conjugate is quenched.
Figure 6B:
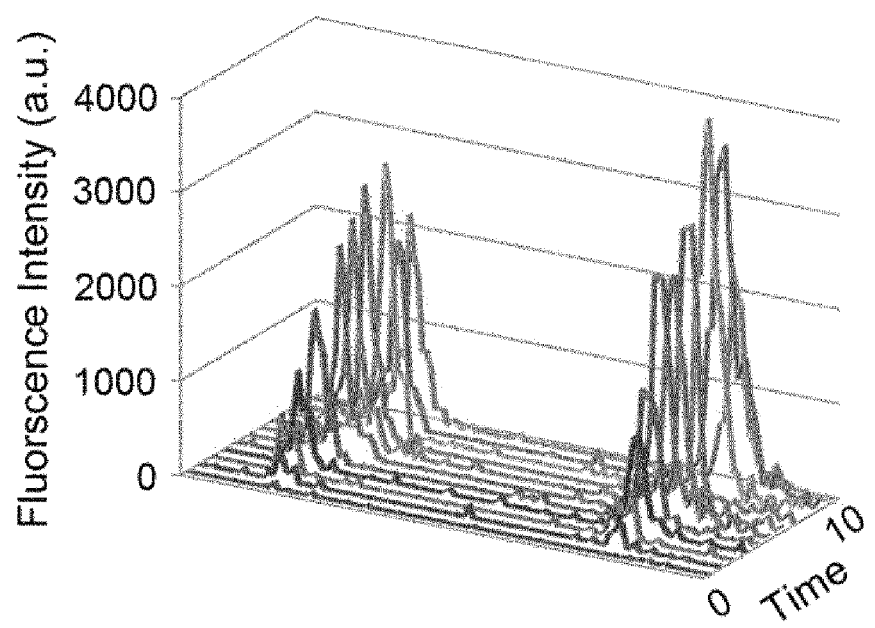
FIG. 6B is a result obtained by analyzing changes in intensity with time of a fluorescent signal emitted from a white line site in FIG. 6A, which is represented by a graph.

According to FIG. 6A, in the SK-BR-3 cancer cell treated with the Trastuzumab-ATTO 680 emittance of a fluorescent signal was initially suppressed and a strong fluorescent signal was emitted on a surface of the cell over time, which made it possible to observe shape and location of the cell. This is a data which supports that fluorescence in the Trastuzumab-ATTO 680 is quenched in a case where the Trastuzumab-ATTO 680 is present on a culture medium other than a cell, and fluorescence emittance is immediately activated in response to binding with an antigen present on a surface of the SK-BR-3 cell so that a location of the cancer cell can be detected through an image without a washing process. In order to quantitatively analyze fluorescence restoration characteristics in FIG. 6A, changes in fluorescence intensity with time at a location of the white line in FIG. 6A were analyzed (FIG. 6B). According to FIG. 6B, it was identified that a fluorescence intensity at a surface of the cell on which an antigen is present is reached to the apex within 5 minutes. This indicates that fluorescent signal activation due to binding with a target antigen occurs very rapidly, and the antibody binds to most of antigens on the surface of the cell within 5 minutes.

Figure 7:
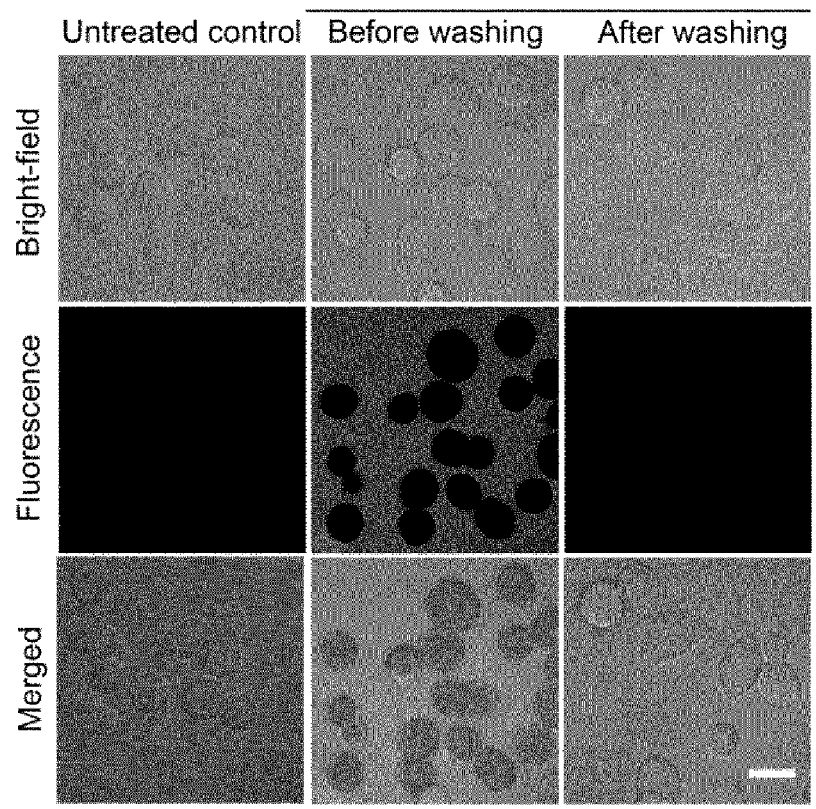
FIG. 7 is data of bright-field image, fluorescent image, and merged image of the former two images before and after washing for a SK-BR-3 cell which has been treated with ATTO 680 which is a fluorescent dye, at a concentration of 1 uM in Example 1 according to the present invention. For comparison, fluorescent images for a SK-BR-3 cell (untreated control) which has not been treated with the fluorescent dye are shown. In a case of being treated with ATTO 680 it can be seen that a strong fluorescent signal was emitted in an extracellular region. After washing, since the fluorescent dye was completely removed, no fluorescent signal was detected in the fluorescent image.

For comparison, results obtained by treating the cancer cell with ATTO 680 which is a free fluorescent dye, at the same concentration, and taking, with fluorescence imaging, states before and after washing are shown in FIG. 7. In a case of being treated with ATTO 680 which is not bound to an antibody, it was found that a strong fluorescent signal was emitted in an extracellular region. After washing, due to removal of all fluorescent dyes, no fluorescent signal was detected in an image. This supports that the result obtained in FIG. 6A is caused by quenching, and shows that ATTO 680 is neither non-specifically adsorbed on a surface of a cancer cell nor endocytosed into the cancer cell.

(5) Analysis of Rate at Which Trastuzumab-ATTO 680 is Endocytosed into Cancer Cells In order to observe time for the Trastuzumab-ATTO 680 which is bound to an antigen (HER2) present on a surface of a cancer cell, to migrate into the cancer cell, SK-BR-3 which is a HER2-overexpressing cancer cell was treated with the Trastuzumab-ATTO 680 at a concentration of 20 ug/mL for 30 minutes. Thereafter, washing was performed three times to remove antibody conjugates in an extracellular region, and fluorescent images were taken over 24 hours to observe a rate at which the antibody conjugate bound to the surface of the cancer cell is endocytosed into the cancer cell.

Figure 8:
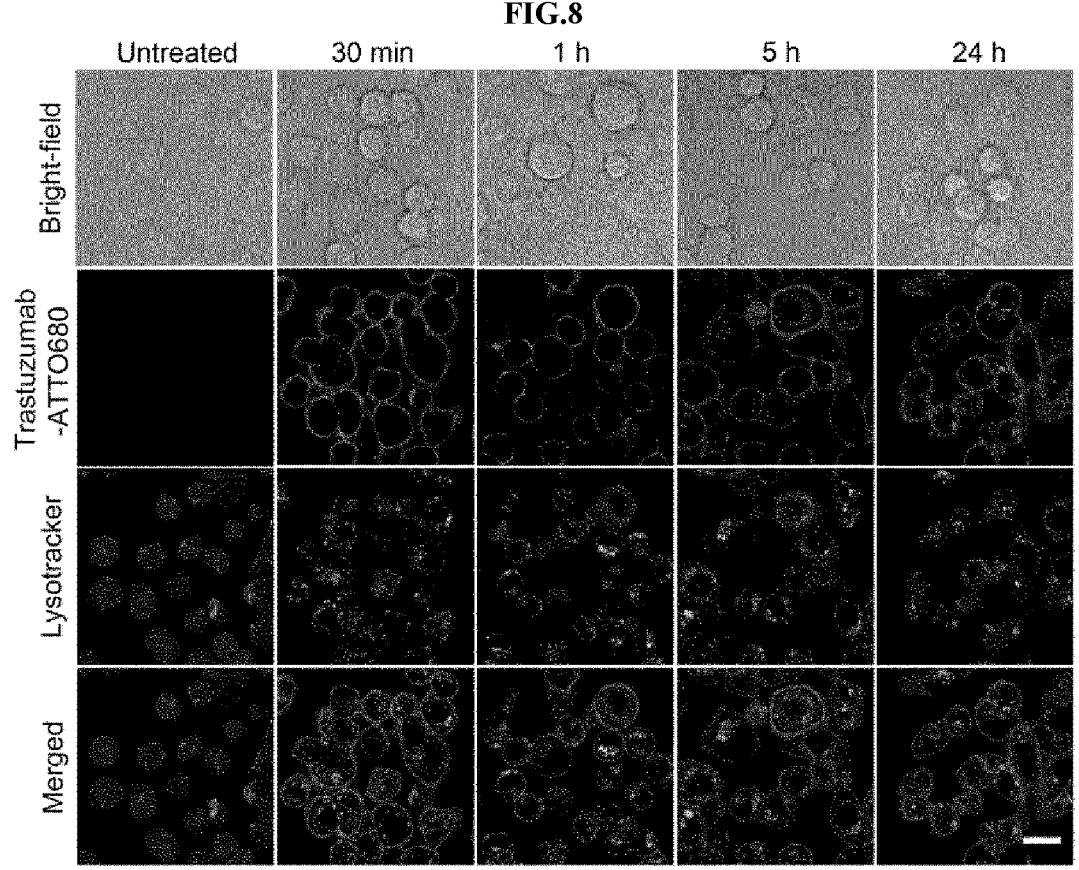
FIG. 8 is fluorescent images obtained by treating HER2-overexpressing cancer cells (SK-BR-3) with the Trastuzumab-ATTO 680 conjugate at a concentration of 10 ug/mL for 30 minutes, removing the unbound Trastuzumab-ATTO 680 conjugate through washing, additionally staining lysosomes with Lysotracker after 1 hour, 5 hours, and 24 hours, respectively, and making an observation in Example 1 according to the present invention. It can be seen that endocytosis of the Trastuzumab-ATTO 680 which is bound to a cell membrane is very slow, and most antibody-fluorescent dye conjugates are located on the cell membranes even after 24 hours.

According to FIG. 8, it can be seen that in a case of SK-BR-3, a considerable number of the antibody-fluorescent dye conjugates which are bound to cell membranes still exist on the surfaces of the cancer cells even after 24 hours. This finding shows that even in a case of cancer cells with a rate at which an antigen present on a surface of the cancer cell is circulated into the cancer cell being slow, in order to obtain an image with high contrast, a fluorescent image has to be obtained by using an antibody-fluorescent dye conjugate in which fluorescence is activated at the time of responding to an antigen present on a cell surface.

(6) Image Performance Evaluation in Xenografted Tumor Animal Model $5 \times 10^6$ each of HER2-positive Calu-3 cancer cells and HER2-negative MDA-MB-231 cancer cells were diluted in 0.1 mL EMEM or RPMI medium, and injected subcutaneously into female athymic nude mice (Balb/c-nu, 5-week old). Then, the mice were measured periodically for tumor cell sizes and used for experiments in a case where tumor sizes reached approximately 190 mm³. For near-infrared fluorescence imaging, Trastuzumab-ATTO 680 (50 ug/50 ul phosphate buffered saline) was intravenously administered to six mice grafted with Calu-3 and MDA-MB-231 tumors. For comparison, mice which are not grafted with tumors were used as another control group, and the same volume of phosphate buffered saline (PBS) was intravenously administered thereto. Near-infrared fluorescent images were taken, using IVIS Lumina imaging equipment, at 1 hour, 5 hours, and 24 hours after intravenous administration ($\lambda$ex.=640/25 nm, $\lambda$em.=732/37 nm).

Figure 9B:
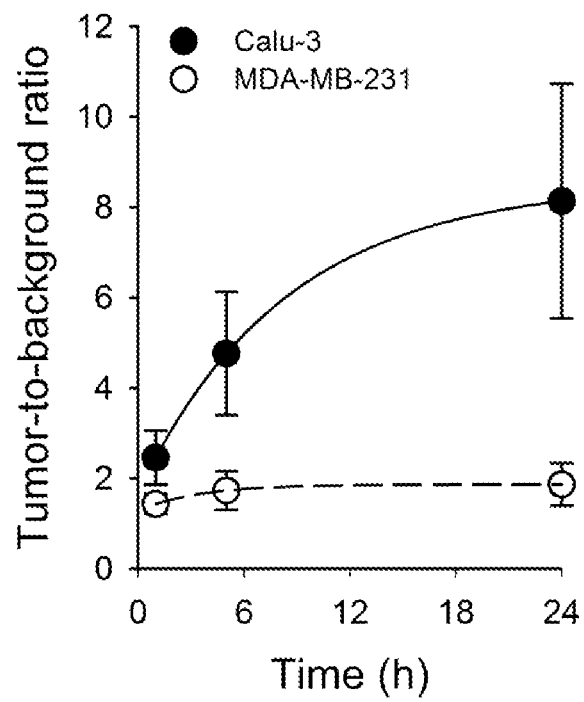
FIG. 9B is data represented by analyzing a tumor-to-background ratio of fluorescent signal with an observation time in the images obtained in FIG. 9A. In a case of HER2-positive Calu-3 tumor-xenografted mice, it can be seen that the tumor-to-background ratio of fluorescent signal is significantly increased over time.

According to FIG. 9A, in a case of mice grafted with the HER2-positive Calu-3 tumor, a location of the tumor could be identified from the fluorescent images at even 1 hour after administration of the Trastuzumab-ATTO 680 and it was found that the location of the tumor was more clearly distinguished over time. On the other hand, in a case of mice grafted with the HER2-negative MDA-MB-231 tumor, it was difficult to distinguish a location of the tumor from a fluorescent image. These results show that the Trastuzumab-ATTO 680 specifically binds to a HER2-positive cancer tissue and fluorescence is activated. According to FIG. 9B, a tumor-to-background ratio analyzed in mice grafted with the HER2-positive Calu-3 tumor was as high as 2.5 (at 1 hour), 4.7 (at 5 hours) and 8.2 (at 24 hours), and a tumor-to-background ratio in mice grafted with the HER2-negative MDA-MB-231 tumor was 1.4 at 1 hour and 1.9 at 24 hours.

(7) Analysis for in Vivo Distribution of Antibody-Fluorescent Dye Conjugate and Accumulation Thereof in Tumor In order to observe in vivo distribution of an intravenously administered antibody-fluorescent dye conjugate, 6 mice grafted with Calu-3 and MDA-MB-231 tumors were intravenously injected with Trastuzumab-ATTO 680 (50 ug/50 ul phosphate buffered saline). Then, tumor tissues, kidneys, spleens, and livers were excised at 1 hour, 5 hours, and 24 hours, and near-infrared fluorescent images were taken ($\lambda$ex.=640/25 nm, $\lambda$em.=732/37 nm).

Figure 9C:
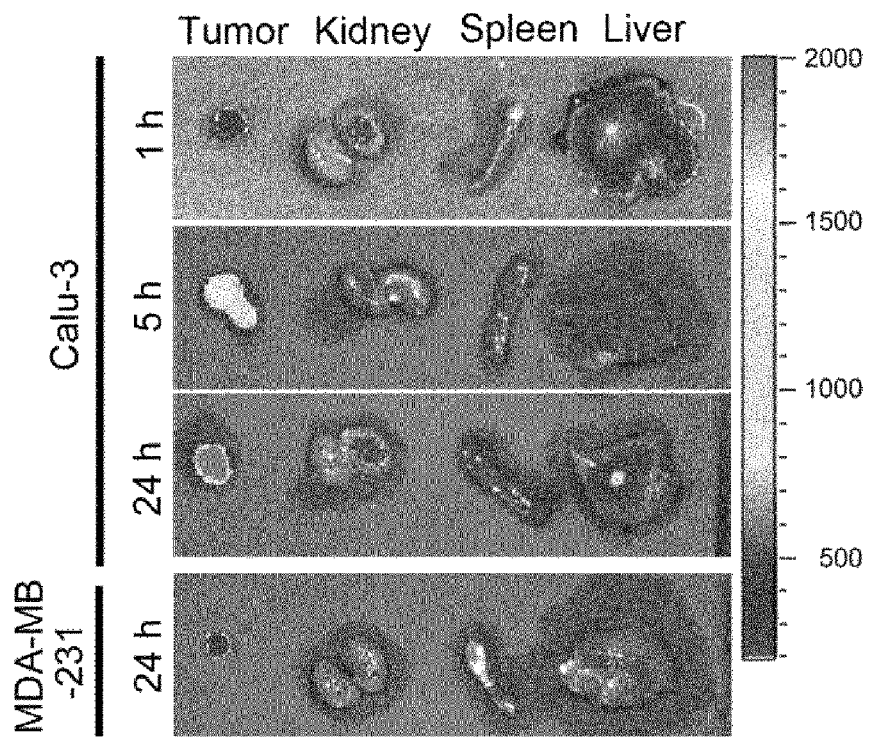
FIG. 9C is a result obtained by administering the Trastuzumab-ATTO 680 conjugate, extracting tumor tissues and organs at each time point, and acquiring near-infrared fluorescent images in Example 1 according to the present invention. In a case of a Calu-3 group, which is an HER2-overexpressing cancer tissue, it can be seen that a strong fluorescent signal is emitted in a tumor.

According to FIG. 9C, it can be identified again that a fluorescent signal in the Calu-3 tumor is increased with time, and it can be seen that a very high signal is obtained from the tumors as compared with other organs such as the livers. It can be identified that antibodies are accumulated at an insignificant level in the MDA-MB-231 tumors.

In addition, tumor tissues obtained at the respective time points after the intravenous administration were immersed in an OCT compound, and frozen tissue sections having a thickness of 7 μm were obtained. Nuclei of cells in the sections were fluorescently stained using a mounting solution containing DAPI. Trastuzumab-ATTO 680 and cells present in the tissue sections were observed through a confocal microscope (Trastuzumab-ATTO 680: $\lambda$ex. 633 nm and $\lambda$em. 647 to 754 nm, DAPI for nuclear staining: $\lambda$ex.=405 nm and $\lambda$em. 420 to 480 nm).

Figure 9D:
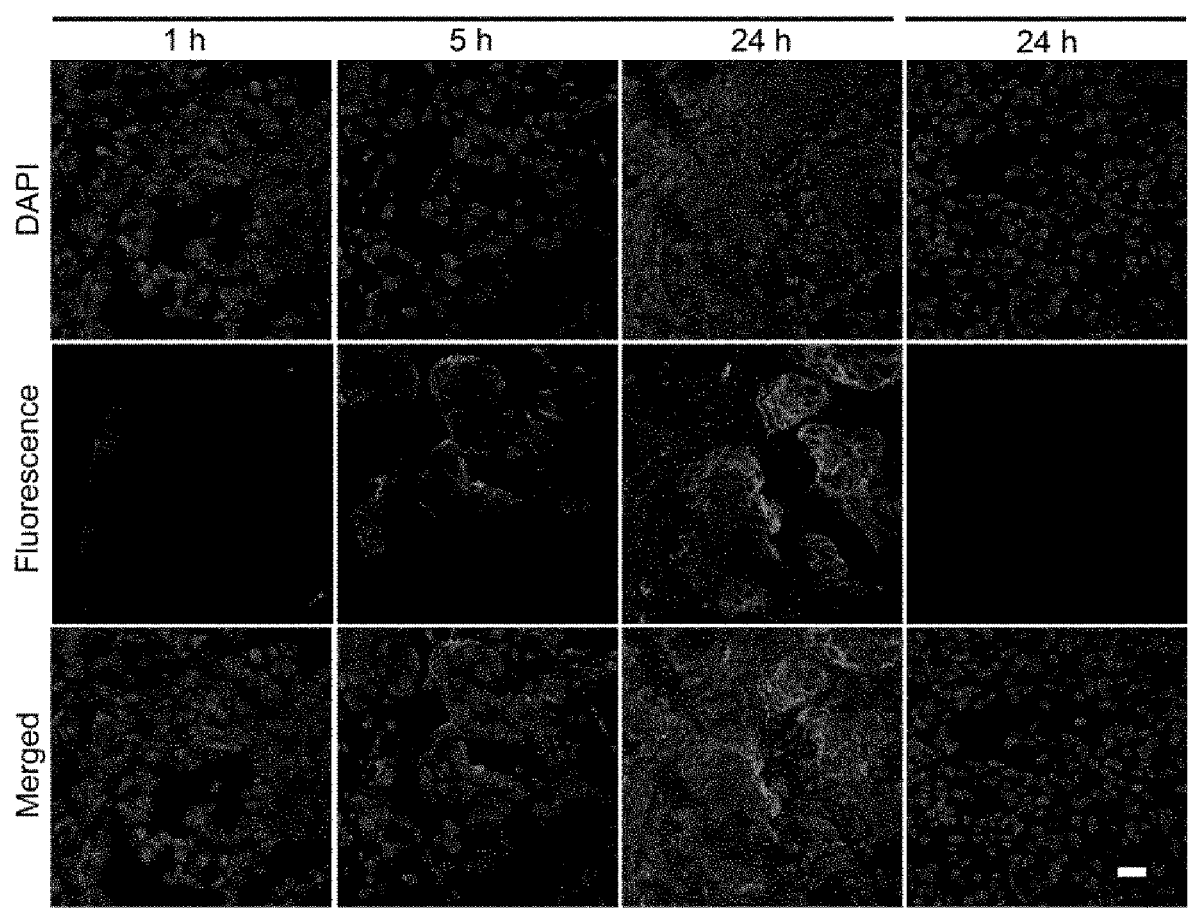
FIG. 9D is a confocal fluorescent image result obtained by administering the Trastuzumab-ATTO 680 conjugate, obtaining a 7 um-thick frozen tissue section for each tumor tissue obtained at each time point, staining nuclei of cancer cells with a DAPI fluorescent dye, and then taking a photograph in Example 1 according to the present invention. A fluorescent signal due to the Trastuzumab-ATTO 680 conjugate was gradually increased over time in cancer tissues, suggesting that a larger amount of the antibody conjugate is bound and accumulates in the cancer tissues as time passes.

Referring to fluorescence photographs for the tumor sections (FIG. 9D), it can be seen that an intensity of a fluorescent signal corresponding to the Trastuzumab-ATTO 680 is gradually increased and expands with time. In the MDA-MB-231 tumors, only a very weak fluorescent signal was detected. This means that the Trastuzumab-ATTO 680 accumulates only in the HER2-positive Calu-3 tumor tissues with time and a near-infrared fluorescent signal is activated.

Example 2

2.1. Synthesis of Cetuximab-ATTO 680 Conjugate

In Example 2, in order to further demonstrate that the basic concept and utility of the antigen responsive-type antibody-fluorescent dye conjugate can be applied to various antibodies, as an example of another antibody, Cetuximab (Erbitux, manufactured by Merck Serono) which is an antibody targeting epidermal growth factor receptor (EGFR) was used to carry out a second embodiment.

It has already been shown in Example 1 that a quenching concept is realized for various fluorescent dyes. Thus, present Example 2 was intended to further verify characteristics and utility of the antigen responsive antibody-fluorescent dye conjugate, by using only ATTO 680 N-hydroxysuccinimidyl ester (ATTO 680-NHS ester) as a fluorescent dye and causing the Cetuximab and the ATTO 680 to react with each other at various ratios. For synthesis of the conjugate, the Cetuximab and the ATTO 680-NHS ester were mixed at a molar ratio of 1:1 or more and dissolved in phosphate buffered saline (PBS, 10 mM, pH 7.4), and then allowed to react at room temperature for 1 hour. Remaining fluorescent dyes that did not react with the antibodies and byproducts were removed with a PD-10 column, and the resultant was concentrated with an Amicon Ultra-0.5 mL filter (EMD Millipore) and stored at 4° C.

2.2. Analysis of Cetuximab-ATTO 680 Conjugate (1) Analysis of Fluorescence-Quenching and Restoration Characteristics A degree of labeling (DL) of the fluorescent dye to Cetuximab was measured by the same method as described in Example 1, and a quenching effect with a degree of labeling was analyzed.

Figure 10A:
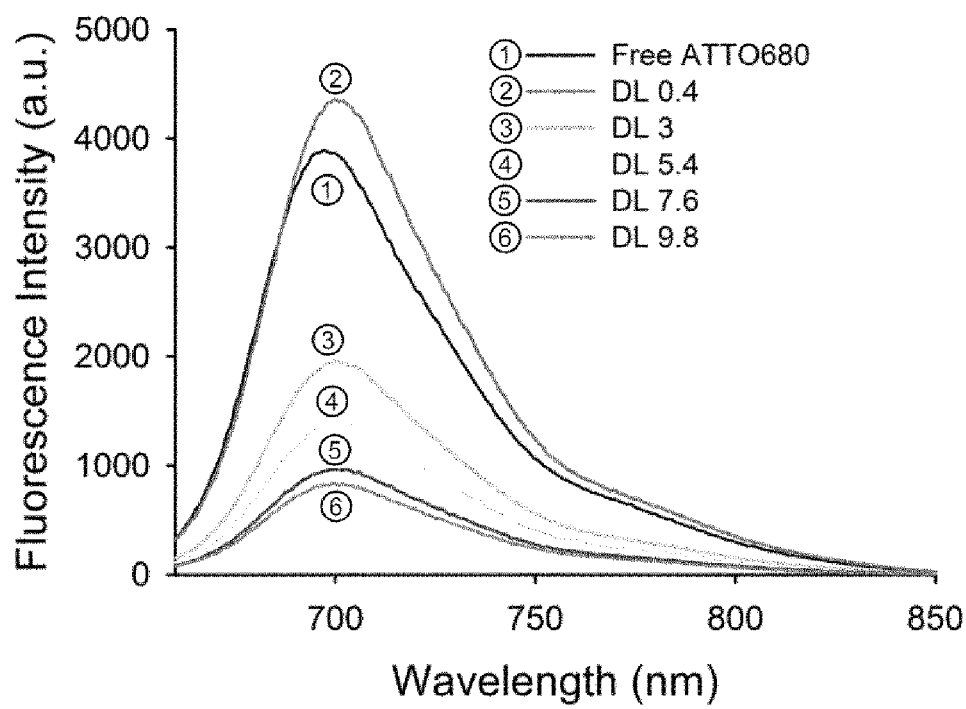
FIG. 10A is fluorescence spectrum (λex. 620 nm, λem. 640 to 850 nm) data with a degree of labeling for the Cetuximab-ATTO 680 conjugate in Example 2 according to the present invention. A fluorescence spectrum of ATTO 680 which is a free fluorescent dye, at the same concentration (1 uM) is shown for comparison.
Figure 10B:
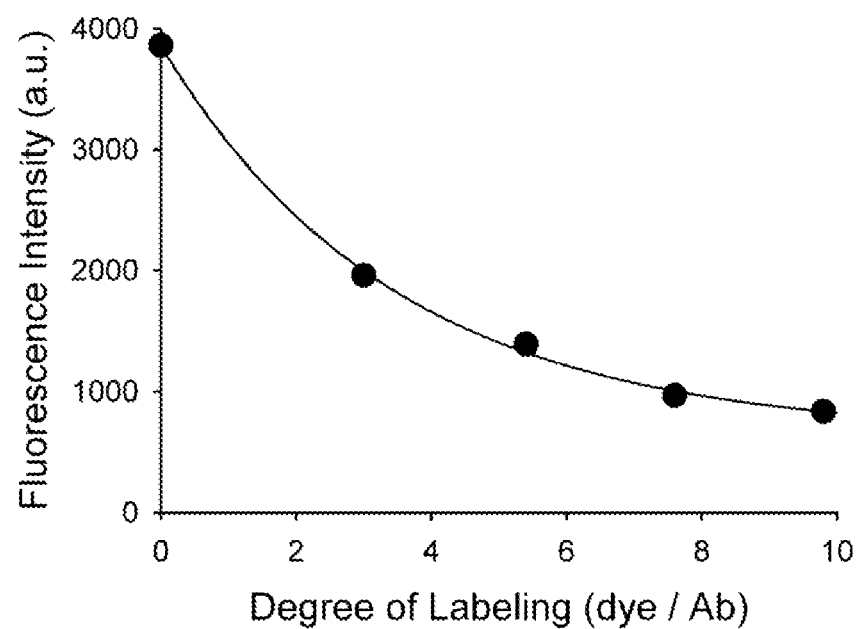
FIG. 10B is a result obtained by analyzing a fluorescence intensity with a degree of labeling for the Cetuximab-ATTO 680 conjugate in Example 2 according to the present invention.

FIGS. 10A and 10B show an extent of quenching with a degree of labeling of the fluorescent dye. As expected, a fluorescence-quenching effect was increased as the degree of labeling was increased, and subsequent experiments proceeded using samples with a degree of labeling of 5.4.

FIG. 10C is a result obtained by treating the Cetuximab-ATTO 680 conjugate (degree of labeling of 5.4) with phosphate buffered saline (PBS) or a denaturing buffer solution (phosphate buffered saline containing 1% sodium dodecyl sulfate (SDS) and 1 mM 2-mercaptoethanol), respectively, and comparing absorbances and fluorescence spectra (λex. 620 nm, and λem. 640 to 850 nm). Referring to FIG. 10C, it was identified that a fluorescent signal of the conjugate was quenched and weakened by 7.6 times as compared with the free dye, and a fluorescence intensity was restored to a level similar to that of the free dye in a case of being treated with the denaturing buffer solution.

(2) Analysis of Antigen Binding Specificity of Cetuximab-ATTO 680 Conjugate

EGFR-negative MCF7 cancer cells and EGFR-positive MDA-MB-468 cancer cell line were treated with the Cetuximab-ATTO 680 conjugate constructed as above at a concentration of 10 ug/mL for 30 minutes, 1 hour, and 2 hours, respectively. Washing was performed to remove antibodies which are not bound to the cells, and then fluorescent images were obtained using a confocal microscope (λex. 633 nm, λem. 647 to 754 nm).

Figure 11B:
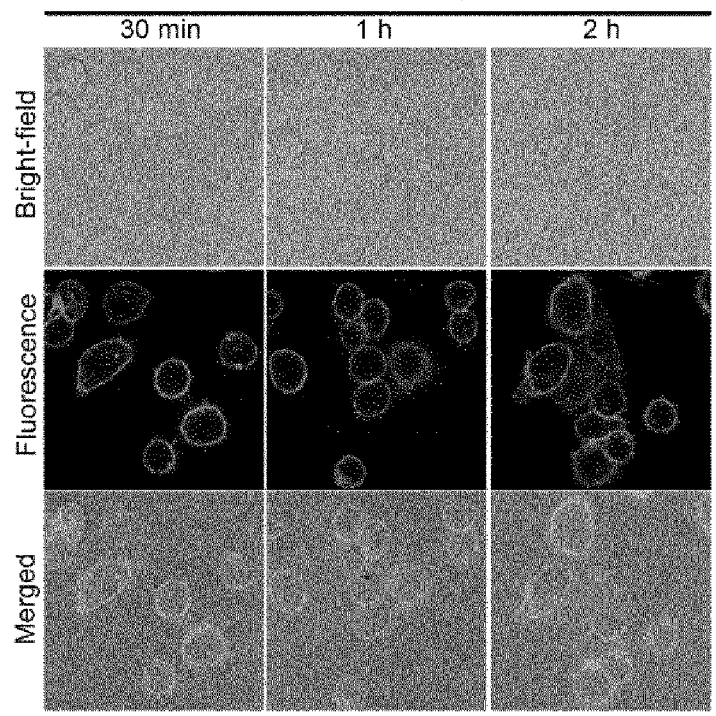
FIG. 11B is a result obtained by treating MDA-MB-468, which is EGFR-positive cancer cells, with the Cetuximab-ATTO 680 conjugate at a concentration of 10 ug/mL for 30 minutes, 1 hour, and 2 hours, respectively, performing washing, and then observing fluorescent images in Example 2 according to the present invention. It can be seen that the Cetuximab-ATTO 680 conjugate specifically binds to the EGFR-positive cancer cells.

According to FIG. 11A, no fluorescent signal was detected in the EGFR-negative MCF-7 even in a case of the 2 hour treatment. A strong fluorescent signal was observed on a cell membrane at 30 minutes in the EGFR-positive MDA-MB-468 (FIG. 11B). These results mean that the Cetuximab-ATTO 680 specifically binds to an EGFR-positive cancer cell and fluorescence that has been quenched is restored again.

(3) Analysis of Endocytosis Rate of Cetuximab-ATTO 680 into Cells

In order to identify an extent of endocytosis of the Cetuximab-ATTO 680 conjugate with time after treating MDA-MB-468 cancer cells therewith, treatment was performed with the Cetuximab-ATTO 680 at a concentration of 20 ug/mL for 30 minutes, washing was performed to remove unbound antibodies, and fluorescent images were observed at 30 minutes, 1 hour, 5 hours, and 24 hours, respectively. As a result, it was found that the conjugates began to migrate into lysosomes in the cells starting from the 5 hours. It was identified that at 24 hours, most of the conjugates were present in the cells, and some of the conjugates were still present on cell membranes (FIG. 12). According to these results, it can be seen that even in a case of EGFR-positive MDA-MB-468 cancer cells, 24 hours is required for the antibody conjugate to sufficiently accumulate in the cells. Therefore, it was found that even in a case of EGFR-positive cancer cells, in order to detect the cancer cells with fluorescence imaging within a short time, the antigen responsive antibody-fluorescent dye conjugate proposed in the present invention are highly suitable rather than using the target cell-specific antibody-fluorescent dye conjugate proposed by Dr. Hisataka Kobayashi.

Example 3

3.1. Synthesis of Anti-VEGF-ATTO 680 Conjugate

In Example 3, in order to further demonstrate that the basic concept and utility of the antigen responsive-type antibody-fluorescent dye conjugate can be applied to various antibodies, as an example of another antibody, anti-VEGF (ab46154, manufactured by Abcam) which targets vascular endothelial growth factor (VEGF) was used to carry out a third embodiment.

It has already been shown in Example 1 that a quenching concept is realized for various fluorescent dyes. Thus, present Example 3 was intended to further verify characteristics and utility of the antigen responsive antibody-fluorescent dye conjugate, by using only ATTO 680 N-hydroxysuccinimidyl ester (ATTO 680-NHS ester) as a fluorescent dye and causing the VEGF antibody and the ATTO 680 to react with each other at various ratios. For synthesis of the conjugate, the VEGF antibody and the ATTO 680-NHS ester were mixed at a molar ratio of 1:1 or more and dissolved in phosphate buffered saline (PBS, 10 mM, pH 7.4), and then allowed to react at room temperature for 1 hour. Remaining fluorescent dyes that did not react with the antibodies and byproducts were removed with a PD-mini Trap G25 column, and the resultant was concentrated with an Amicon Ultra-0.5 mL filter (EMD Millipore, 30 kDa) and stored at 4° C.

3.2 Analysis of Anti-VEGF-ATTO 680 Conjugate (1) Analysis of Fluorescence-Quenching and Restoration Characteristics A degree of labeling (DL) of the fluorescent dye to the VEGF antibody was measured by the same method as described in Example 1, and a quenching effect with a degree of labeling was analyzed.

Figure 13A:
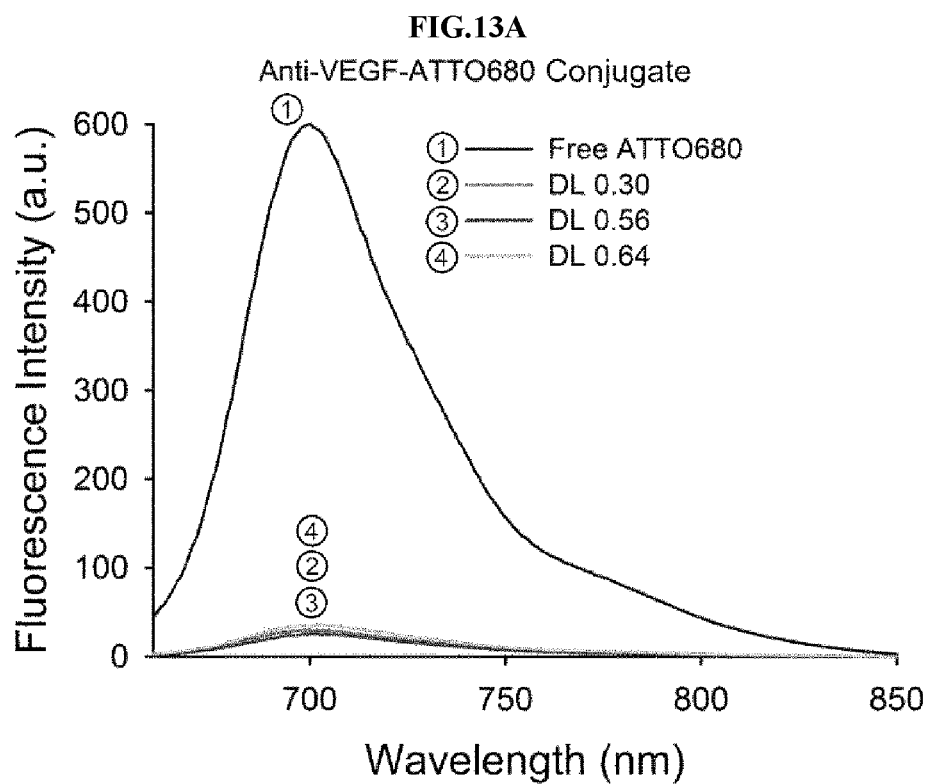
FIG. 13A is fluorescence spectrum (λex. 620 nm, λem. 640 to 850 nm) data with a degree of labeling for the anti-VEGF-ATTO 680 conjugate in Example 3 according to the present invention. A fluorescence spectrum of ATTO 680 which is a free fluorescent dye, at the same concentration (0.1 uM) is shown for comparison.
Figure 13B:
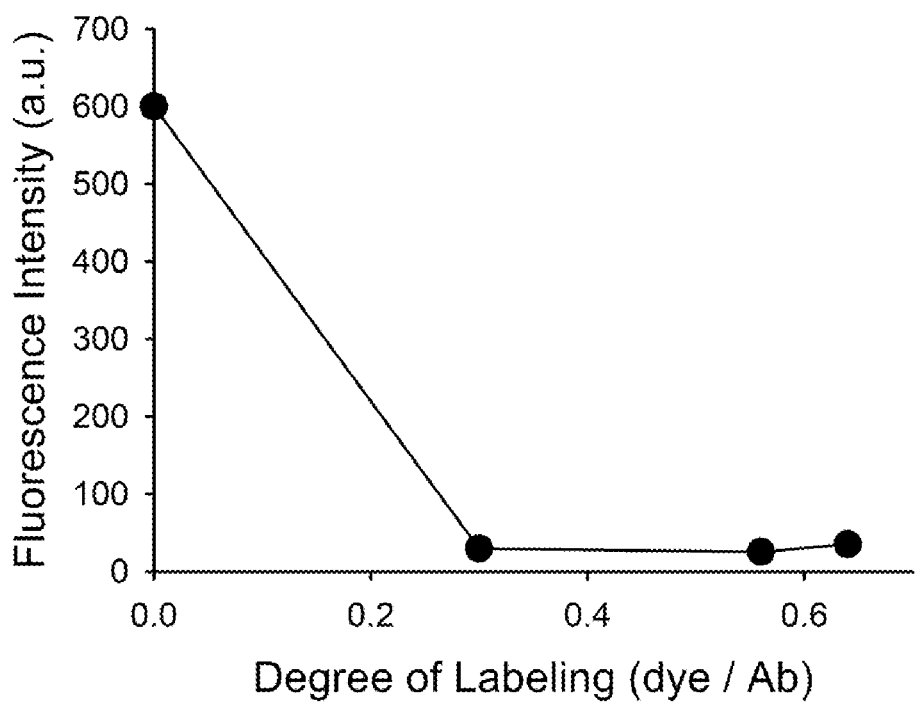
FIG. 13B is a result obtained by analyzing a fluorescence intensity with a degree of labeling for the anti-VEGF-ATTO 680 conjugate in Example 3 according to the present invention.

FIGS. 13A and 13B show an extent of quenching with a degree of labeling of the fluorescent dye. As expected, it was found that a fluorescence-quenching effect was increased as the degree of labeling was increased.

Example 4

4.1. Synthesis of Anti-Vimentin-ATTO 680 Conjugate

In Example 4, as an example of another antibody for further demonstrating that the basic concept and utility of the antigen responsive-type antibody-fluorescent dye conjugate can be applied to various antibodies, anti-Vimentin (ab92547, manufactured by Abcam) which targets Vimentin, which is a cytoskeletal marker expressed in a case where a skeleton of a tumor cell is changed for ease of migration at the time of tumor metastasis, was used to carry out a fourth embodiment.

It has already been shown in Example 1 that a quenching concept is realized for various fluorescent dyes. Thus, present Example 4 was intended to further verify characteristics and utility of the antigen responsive antibody-fluorescent dye conjugate, by using only ATTO 680 N-hydroxysuccinimidyl ester (ATTO 680-NHS ester) as a fluorescent dye and causing the Vimentin antibody and the ATTO 680 to react with each other at various ratios. For synthesis of the conjugate, the Vimentin antibody and the ATTO 680-NHS ester were mixed at a molar ratio of 1:1 or more and dissolved in phosphate buffered saline (PBS, 10 mM, pH 7.4), and then allowed to react at room temperature for 1 hour. Remaining fluorescent dyes that did not react with the antibodies and byproducts were removed with a PD-mini Trap G25 column, and the resultant was concentrated with an Amicon Ultra-0.5 mL filter (EMD Millipore, 30 kDa) and stored at 4° C.

4.2. Analysis of Anti-Vimentin-ATTO 680 Conjugate (1) Analysis of Fluorescence-Quenching and Restoration Characteristics A degree of labeling (DL) of the fluorescent dye to the Vimentin antibody was measured by the same method as described in Example 1, and a quenching effect with a degree of labeling was analyzed.

Figure 14A:
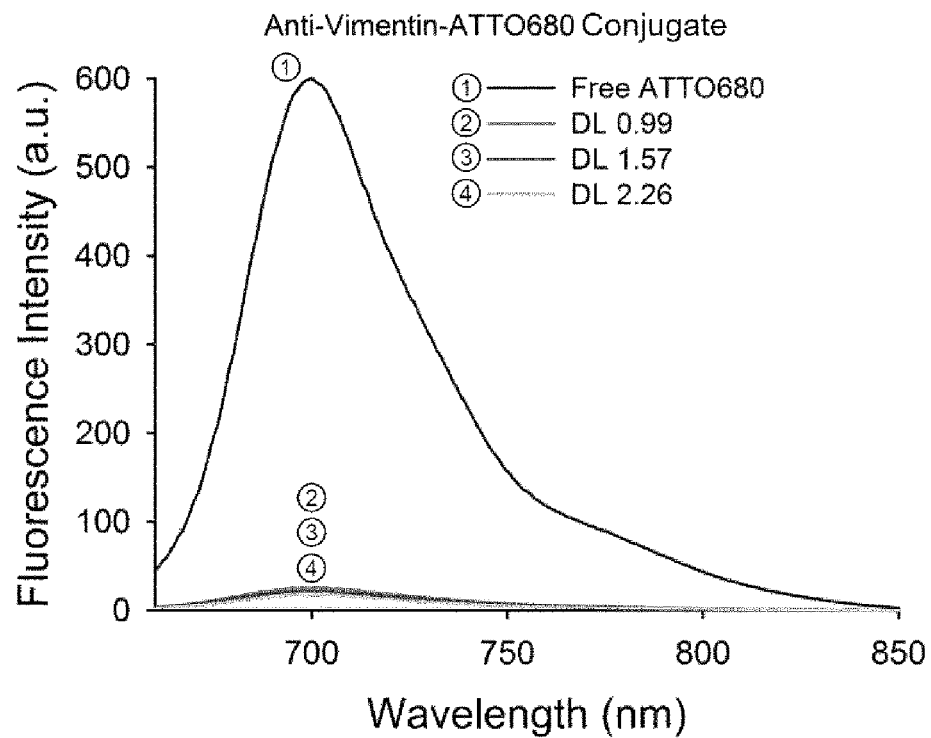
FIG. 14A is fluorescence spectrum (λex. 620 nm, λem. 640 to 850 nm) data with a degree of labeling for the anti-Vimentin-ATTO 680 conjugate in Example 4 according to the present invention. A fluorescence spectrum of ATTO 680 which is a free fluorescent dye, at the same concentration (0.1 uM) is shown for comparison.
Figure 14B:
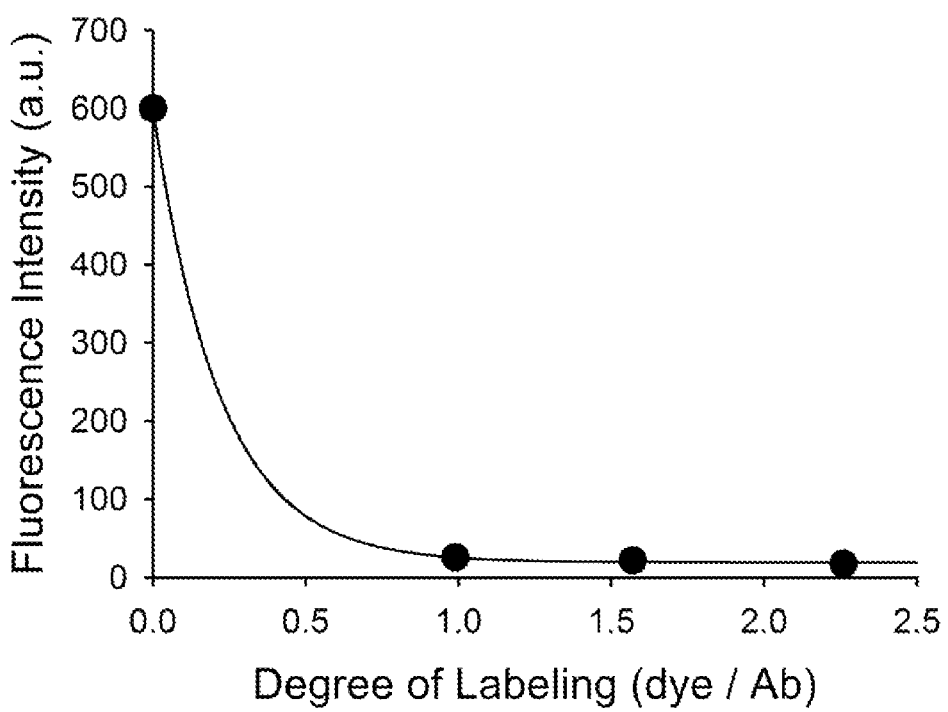
FIG. 14B is a result obtained by analyzing a fluorescence intensity with a degree of labeling for the anti-Vimentin-ATTO 680 conjugate in Example 4 according to the present invention.

FIGS. 14A and 14B show an extent of quenching with a degree of labeling of the fluorescent dye. As expected, it was found that a fluorescence-quenching effect was increased as the degree of labeling was increased.

Example 5

5.1. Synthesis of Anti-CD44-ATTO 680 Conjugate

In Example 5, as an example of another antibody for further demonstrating that the basic concept and utility of the antigen responsive-type antibody-fluorescent dye conjugate can be applied to various antibodies, a CD44 antibody (AF3660, manufactured by R&D Systems which targets CD44, which is one of transmembrane proteins involved in cell to cell and cell to substrate communication, was used to carry out a fifth embodiment.

It has already been shown in Example 1 that a quenching concept is realized for various fluorescent dyes. Thus, present Example 5 was intended to further verify characteristics and utility of the antigen responsive antibody-fluorescent dye conjugate, by using only ATTO 680 N-hydroxysuccinimidyl ester (ATTO 680-NHS ester) as a fluorescent dye and causing the CD44 antibody and the ATTO 680 to react with each other at various ratios. For synthesis of the conjugate, the CD44 antibody and the ATTO 680-NHS ester were mixed at a molar ratio of 1:1 or more and dissolved in phosphate buffered saline (PBS, 10 mM, pH 7.4), and then allowed to react at room temperature for 1 hour. Remaining fluorescent dyes that did not react with the antibodies and byproducts were removed with a PD-mini Trap G25 column, and the resultant was concentrated with an Amicon Ultra-0.5 mL filter (EMD Millipore, 30 kDa) and stored at 4° C.

5.2. Analysis of Anti-CD44-ATTO 680 Conjugate (1) Analysis of Fluorescence-Quenching and Restoration Characteristics A degree of labeling (DL) of the fluorescent dye to the CD44 antibody was measured by the same method as described in Example 1, and a quenching effect with a degree of labeling was analyzed.

Figure 15A:
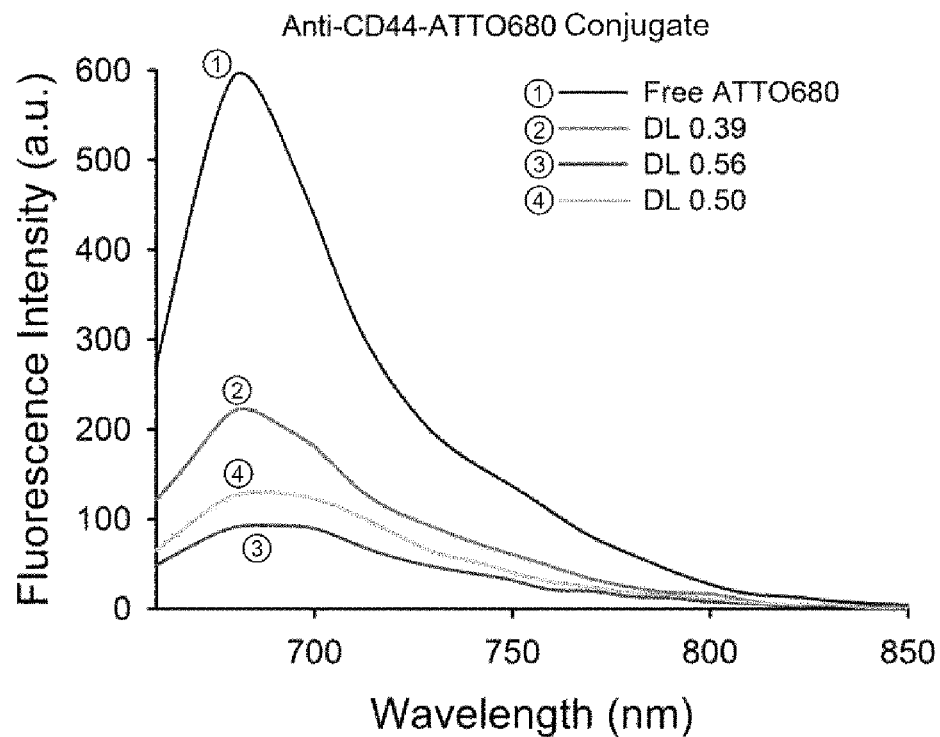
FIG. 15A is fluorescence spectrum (λex. 620 nm, λem. 640 to 850 nm) data with a degree of labeling for the anti-CD44 (8E2)-ATTO 680 conjugate in Example 5 according to the present invention. A fluorescence spectrum of ATTO 680 which is a free fluorescent dye, at the same concentration (0.1 uM) is shown for comparison.
Figure 15B:
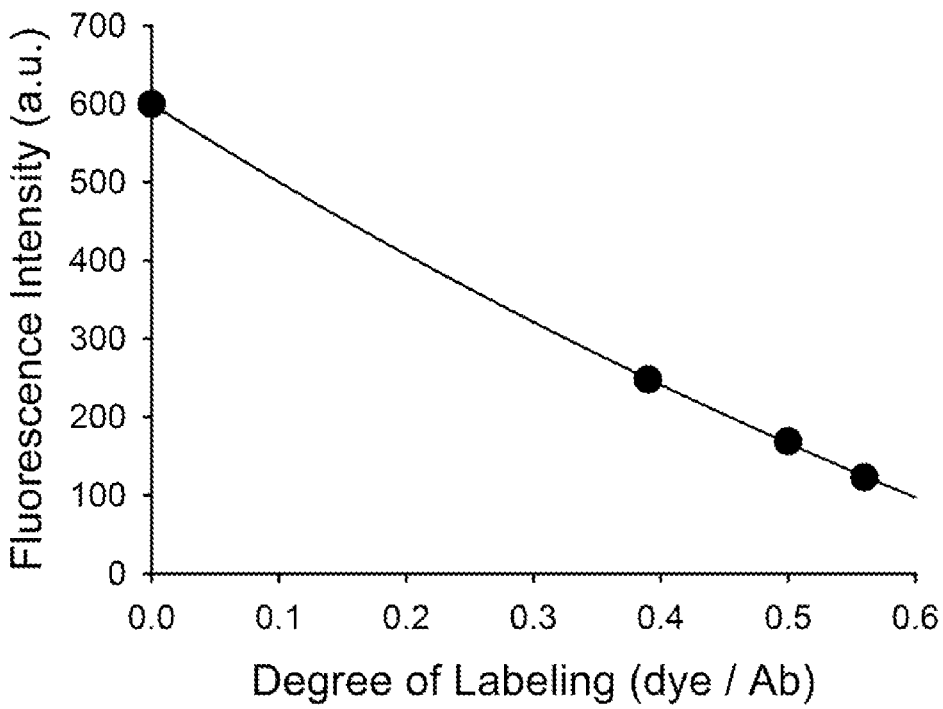
FIG. 15B is a result obtained by analyzing a fluorescence intensity with a degree of labeling for the anti-CD44 (8E2)-ATTO 680 conjugate in Example 5 according to the present invention.

FIGS. 15A and 15B show an extent of quenching with a degree of labeling of the fluorescent dye. As expected, it was found that a fluorescence-quenching effect was increased as the degree of labeling was increased.

Certain parts of the present invention have been described in detail as above. However, it will be apparent to those skilled in the art that such a specific description is merely a preferred embodiment, and the scope of the present invention is not limited thereby. Accordingly, the actual scope of the present invention will be defined by the appended claims and equivalents thereof.

The invention claimed is:

1. A composition for diagnosing or detecting target cells through fluorescence imaging, comprising, as an active ingredient:

an antigen responsive antibody-fluorescent dye conjugate which allows imaging diagnosis of a cell having a target antigen on a surface of a cell membrane, wherein the fluorescent dye is labeled in a constant region of the antibody through a covalent bond with an antibody, wherein the fluorescent dye is quenched by photo-induced electron transfer(PET) with a residue selected from the group consisting of tryptophan, tyrosine, histidine, and methionine in the antibody, and is dequenched to emit fluorescence on the surface of the cell membrane as a distance between the fluorescent dye and the residue selected from the group consisting of tryptophan, tyrosine, histidine, and methionine in the antibody increases due to a three-dimensional conformational change of the antibody that occurs in a case where the antibody binds to the antigen present on the surface of the cell membrane, wherein the fluorescent dye is one selected from ATTO 655, ATTO 680, ATTO 700, ATTO MB2, and ZW800-1, wherein the fluorescent dye has a formula selected from the group consisting of:

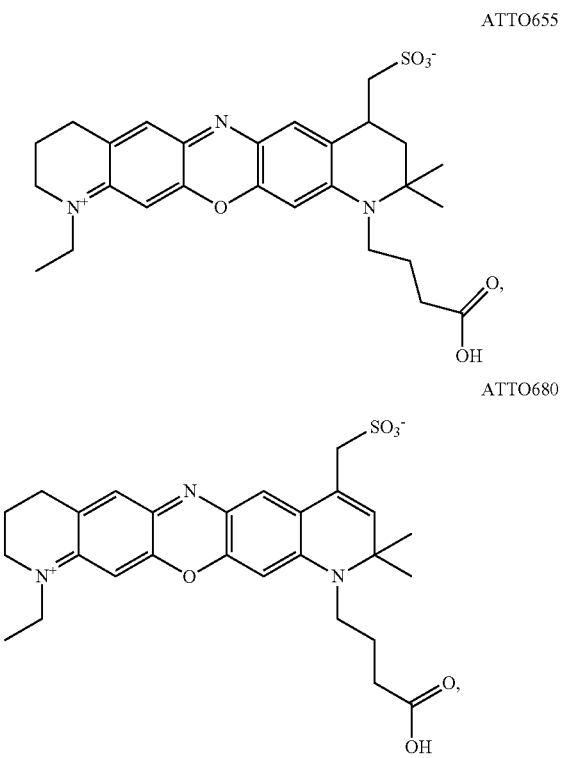

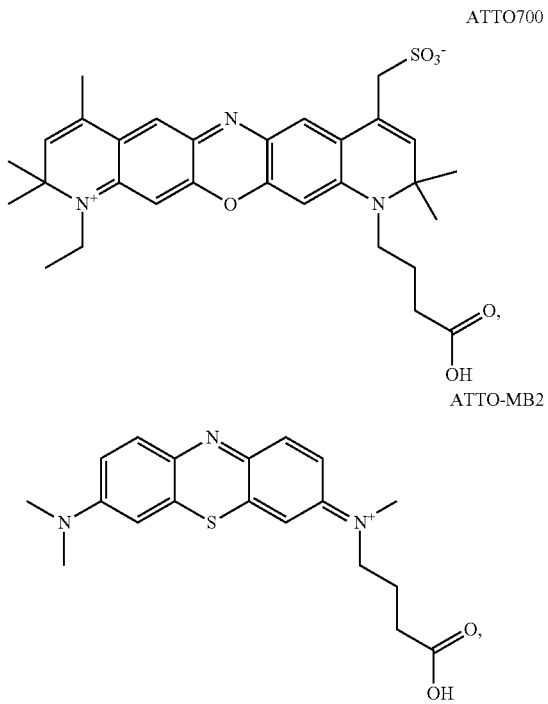

ATTO700

ATTO-MB2 and

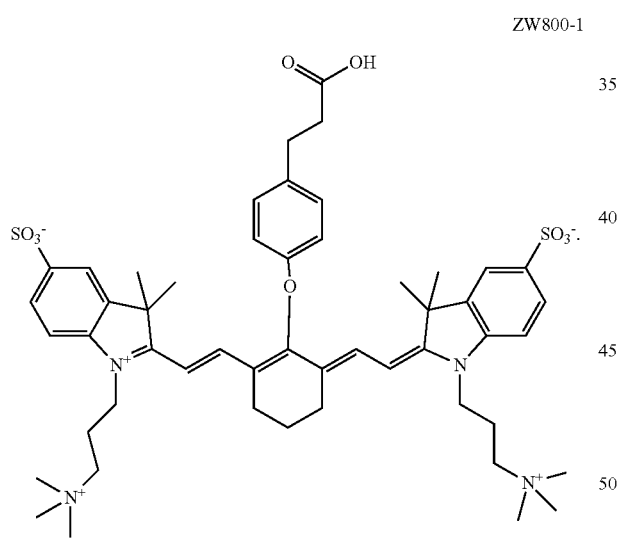

ZW800-1

2. The composition according to claim 1, wherein the antigen to which the antibody binds is selected from the group consisting of epidermal growth factor receptor (EGFR, HER1), human epidermal growth factor receptor 2 (HER2), human epidermal growth factor receptor 3 (HER3, ERBB-3), human epidermal growth factor receptor 4 (HER4, ERBB-4), epithelial cell adhesion molecule (Ep-Cam), CD19, CD20, CD22 (Siglec-2), CD30 (TNFRSF1), CD33 (Siglec-3), CD44, CD44v6, CD52, CD56 (NCAM), CD152 (CTLA4), mucin 1 (MUC1), carcinoembryonic antigen (CEA), LEWIS Y, prostate-specific membrane antigen (PSMA), tumor-associated glycoprotein 72 (TAG-72), GD2 ganglioside, GD3 ganglioside, human leukocyte antigen-DR10 (HLA-DR10), insulin-like growth factor 1 receptor (IGF1R), tumor-associated antigen L6 (TAL6), tumor-necrosis factor-related apoptosis-inducing ligand receptor 2 (TRAILR2), vascular endothelial growth factor (VEGF), vascular endothelial growth factor receptor 2 (VEGFR2), platelet-derived growth factor receptor alpha (PDGFRA), hepatocyte growth factor receptor (HGFR), Alpha-v beta-3, Folate receptor, EGF-like domain-containing protein 7 (EGFL7), Fibroblast activation protein alpha (FAP), Carbonic anhydrase 9 (CA9/CA1X), and Vimentin.

3. The composition according to claim 1,
wherein the antibody is selected from the group consisting of: Cetuximab, Panitumumab, Necitumumab, Imgatuzumab, Matuzumab, Nimotuzumab, Futuximab, and Zalutumumab which are antibodies to EGFR; Trastuzumab and Pertuzumab which are antibodies to HER2; Duligotumab, Patritumab, and Seribantumab which are antibodies to HER3; Bevacizumab which is an antibody to VEGF-A; Catumaxomab and Adecatumumab (MT201) which are antibodies to EpCam; Cixutumumab (IMC-Al2), Figitumumab, Ganitumab, Robatumuma, Teprotumumab, and Dalotuzumab which are antibodies to IGF1R; Conatumumab (AMG 655), Drozitumab, Lexatumumab, and Tigatuzumab which are antibodies to TRAILR2; Rituximab, Ibritumomab tiuxetan, Tositumomab, Ofatumumab, Ocaratuzumab, Ublituximab, and Obinutuzumab which are antibodies to CD20; Epratuzumab, Inotuzumab, and Narnatumab which are antibodies to CD22;

Brentuximab and Iratumumab which are antibodies to CD30; Gentuzumab and Lintuzumab which are antibodies to CD33; Bivatuzumab which is an antibody to CD44v6; Alemtuzumab which is an antibody to CD52; Dinutuximab which is an antibody to GD2 ganglioside; Ecromeximab which is an antibody to GD3 ganglioside; Olaratumab which is an antibody to platelet-derived growth factor receptor alpha (PDGFRA); Emibetuzumab which is an antibody to hepatocyte growth factor receptor (HGFR); Etaracizumab which is an antibody to Alpha-v beta-3; Farletuzumab which is an antibody to Folate receptor alpha; Parsatuzumab which is an antibody to EGF-like domain-containing protein 7 (EGFL7); Sibrotuzumab which is an antibody to Fibroblast activation protein alpha (FAP); Girentuximab which is an antibody to Carbonic anhydrase 9 (CA9/CAIX); anti-CD44; and anti-Vimentin.

4. The composition according to claim 1,
wherein the composition is a formulation for injection or a formulation for spraying.

5. A method for providing information for target cells or cancer diagnosis through imaging, the method comprising:
administering the composition of claim 1 to a patient having cancer; and
imaging the composition in the patient to detect or measure a tumor factor.

6. A method for providing information for target cells or cancer diagnosis through imaging, the method comprising:
administering the composition of claim 2 to a patient having cancer; and
imaging the composition in the patient to detect or measure a tumor factor.

7. A method for providing information for target cells or cancer diagnosis through imaging, the method comprising:
administering the composition of claim 3 to a patient having cancer; and imaging the composition in the patient to detect or measure a tumor factor.

* * * * *